US008034549B2

(12) United States Patent
Kruk

(10) Patent No.: US 8,034,549 B2
(45) Date of Patent: Oct. 11, 2011

(54) DETECTION OF CANCER BY ELEVATED LEVELS OF BCL-2

(75) Inventor: Patricia A. Kruk, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 11/704,408

(22) Filed: Feb. 9, 2007

(65) Prior Publication Data

US 2008/0009005 A1     Jan. 10, 2008

Related U.S. Application Data

(60) Provisional application No. 60/771,677, filed on Feb. 9, 2006.

(51) Int. Cl.
C12Q 1/00      (2006.01)
G01N 33/574   (2006.01)
(52) U.S. Cl. ............................. 435/4; 435/7.23; 435/7.1
(58) Field of Classification Search .................. None
See application file for complete search history.

(56) References Cited

U.S. PATENT DOCUMENTS

| | | | |
|---|---|---|---|
| 5,015,568 A | 5/1991 | Tsujimoto et al. | |
| 5,459,251 A | 10/1995 | Tsujimoto et al. | |
| 5,506,344 A | 4/1996 | Tsujimoto et al. | |
| 5,523,393 A | 6/1996 | Tsujimoto et al. | |
| 5,595,869 A | 1/1997 | Tsujimoto et al. | |
| 5,641,866 A | 6/1997 | Reed et al. | |
| 6,130,201 A | 10/2000 | Croce et al. | |
| 6,207,452 B1 | 3/2001 | Govindaswamy | |
| 2002/0106731 A1 | 8/2002 | Ruben et al. | |
| 2004/0137538 A1* | 7/2004 | Bradford ...................... | 435/7.23 |

FOREIGN PATENT DOCUMENTS

| | | |
|---|---|---|
| KR | 10-2003-0092378 A | 12/2003 |
| RU | 2262939 C2 | 10/2005 |
| WO | WO-01-11361 A2 | 2/2001 |
| WO | WO-02/090931 A2 | 11/2002 |
| WO | WO-03-078662 A1 | 9/2003 |

OTHER PUBLICATIONS

Kibel, AS et al, 2000, J urol, 164(1): 192-6.*
Dong et al, 2000, Cancer Research, 60: 3880-3883.*
Zhau, HE, 1994, J Cell Biochem, Suppl 19: 208-216.*
Ren, C et al, 1998, Cancer Res, 58(6): 1285-90.*
Gingrich, JR et al, 1996, Cancer res, 56(18): 4096-4102.*
Russo, V et al, 1995, Int J Cancer, 64: 216-221.*
Li et al, 2005, Arch Gynecol Obstet, 272: 48-52.*
Tas et al, Jun. 2006, Medical Oncol, 23(2): 213-217.*
Ohkaru et al, 1995, J Immunol method, 178: 99-111.*
Ackermann, E. J. et al., "The Role of Antiapoptotic Bcl-2 Family Members in Endothelial Apoptosis Elucidated with Antisense Oligonucleotides" *J. Biol. Chem.*, 1999, 274:11245-11252.
Farrow, S.N. and Brown, R. "New members of the Bcl-2 family and their protein partners" *Curr. Opin. Gen. Dev.*, 1996 6:45-49.
Hanaoka, T. et al., "Immunohistochemical demonstration of apoptosis-regulated proteins, Bcl-2 and Bax, in resected non-small-cell lung cancers" *Intl. J. Clin. Oncol.*, 2002, 7:152-158.
Khalifeh, I. et al., "Expression of Cox-2, CD34, Bcl-2, and p53 and Survival in Patients with Primary Peritoneal Serous Carcinoma and Primary Ovarian Serous Carcinoma" *Int. J. Gynecol. Pathol.*, 2004, 23:162-169.
Lickliter, J.D et al. "HA14-1 selectively induces apoptosis in Bcl-2-overexpressing leukemia/lymphoma cells, and enhances cytarabine-induced cell death" *Leukemia*, 2003, 17:2074-2080.
O'Neill, C.J. et al. "An Immunohistochemical Comparison Between Low-Grade and High-Grade Ovarian Serous Carcinomas" *Am, J. Surg. Pathol.*, 2005 29:1034-1041.
Sharma, H. et al. "Combined evaluation of expression of telomerase, surviving, and anti-apoptotic Bcl-2 family members in relation to loss of differentiation and apoptosis in human head and neck cancers" *Head Neck*, 2004, 26:733-740.
Thomenius, M.J. and Distelhorst, C.W. "Bcl-2 on the endoplasmic reticulum: protecting the mitochondria from a distance" *J. Cell Sci.*, 2003, 116:4493-44990.
Trisciuoglio, D. et al. "Bcl-2 Overexpression in Melanoma Cells Increases Tumor Progression-Associated Properties and in Vivo Tumor Growth" *J. Cell Physiol.*, 2005, 205:414-421.
Eissa, S. et al. "Quantitation of bcl-2 protein in bladder cancer tissue by enzyme immunoassay: comparison with Western blot and immunohistochemistry" *Clinical Chemistry*, 1998, 44(7): 1423-1429.
Hussain, S. A. et al. "BCL2 expression predicts survival in patients receiving synchronous chemoradiotherapy in advanced transitional cell carcinoma of the bladder" *Oncology Reports*, 2003, 10: 571-576.
Friedrich, M. G. et al. "Detection of Methylated Apoptosis-Associated Genes in Urine Sediments of Bladder Cancer Patients" *Clinical Cancer Research*, 2004, 10: 7457-7465.
Ziaee, S. A. et al. "Diagnosis of Bladder Cancer by Urine Survivin, an Inhibitor of Apoptosis" *Urological Oncology*, 2006, 3(3): 150-153.
Abramenko, I.V. and Filchenkov, A.A. "Evaluation of apopotosis and diagnosis of cancer, prognosis and improvement of therapy" *Voprosy Onkologii* (St. Petersburg), 2003, 49(1):21-30, abstract.
Cao, Y. et al. "Elevated levels of urine angiostatin and plasminogen/plasmin in cancer patients" *Int. J Mol Med*, 2000, 5:547-551.
Smith, S.D. et al. "Urine Detection of Survivin and Diagnosis of Bladder Cancer" *JAMA*, 2001, 285:324-328.

(Continued)

*Primary Examiner* — Misook Yu
*Assistant Examiner* — Lei Yao
(74) *Attorney, Agent, or Firm* — Saliwanchik, Lloyd & Eisenschenk

(57) ABSTRACT

The present invention relates to a method for the diagnosis, prognosis, and monitoring of cancer, such as early or late stage ovarian cancer, in a subject by detecting Bcl-2 in a biological sample from the subject, preferably a urine or blood sample. Bcl-2 may be measured using an agent that detects or binds to Bcl-2 protein or an agent that detects or binds to encoding nucleic acids, such as antibodies specifically reactive with Bcl-2 protein or a portion thereof. The invention further relates to kits for carrying out the methods of the invention. The invention further relates to a device for the rapid detection of Bcl-2 in a bodily fluid and methods for rapidly measuring Bcl-2 in a bodily fluid.

17 Claims, 14 Drawing Sheets

OTHER PUBLICATIONS

Johnson, N. C. et al. "Detection of Bcl-2 and Survivin in Urine and Imidazome-treated Plasma for Ovarian Disease" presented at the University of South Florida Health Sciences Research Day, Feb. 26, 2004, pp. 1-8.

Johnson, N. C. et al. "Screening plasma and urine from women with ovarian disease for Bcl-2, survivin and telomerase" *Proc Amer Assoc Cancer Res*, 2004, vol. 45, Abstract #1339.

Kruk, P.A. "Detection of ovarian cancer by elevated urinary levels of Bcl-2" 97th Annual Meeting for the American Association for Cancer Research, Washington, DC, Apr. 1-5, 2006.

Kruk, P.A. "Analysis of Biomarkers in Ovarian Cancer" Biomedical Engineering Seminar Series, University of South Florida, Tampa, FL, Feb. 17, 2006.

Kruk, P.A. et al. "Detection of Ovarian Cancer by Elevated Urinary Levels of Bcl-2" 6th Biennial Ovarian Cancer Research Symposium, Seattle, WA, Sep. 8, 2006.

Kruk, P.A. et al. "Detection of Ovarian Cancer by Elevated Urinary Levels of Bcl-2" *Proc Amer Assoc Cancer Res*, 2006, vol. 47, Abstract #2418.

Tools for the Study of Apoptosis, pp. 1-25, Chemicon International, Inc.

Bcl-2 Sandwich ELISA KIT, pp. 1-10, Chemicon International, Inc.

Bcl 2 (B Cell Leukemia 2) BioAssay™ ELISA kit, pp. 1-2, retrieved: Jan. 23, 2007 from.

Bcl-2 Antibody, pp. 1-2, 2005, Cell Signaling Technology, Inc.

Bcl-2 Antibody (Human Specific), pp. 1-3, 2005, Cell Signaling Technology, Inc.

Product Information and Manual, human Bcl-2 ELISA BMS244/3 Enzyme-linked immunosorbent assay for quantitative detection of human Bcl-2, pp. 2-32, Jul. 28, 2005, Bender MedSystems GmbH, Campus Vienna Biocenter 2, Vienna, Austria, Europe.

Tas, F. et al., "The Value of Serum bcl-2 Levels in Advanced Epithelial Ovarian Cancer." *Medical Oncology*, 2006, 23: 213-217.

Giannoulis, K. et al. (2004). Serum levels of bcl-2 in patients with colorectal cancer. *Techniques in Coloproctology*, 8(Supplement 1): S56-S58.

Office Action dated Feb. 22, 2011 in Russian Application No. 2008136193, filed Feb. 9, 2007.

Henriken, R. et al. (1995). Expression and prognostic significance of Bcl-2 in ovarian tumours. *British Journal of Cancer*, 72: 1324-1329.

Herod, J. J. O. et al. (1996). The Prognostic Significance of Bcl-2 and p53 Expression in Ovarian Carcinoma. *Cancer Research*, 56: 2178-2184.

English translation of Office Action dated Jul. 5, 2011 in Japanese Application No. 2008-554404, filed Feb. 9, 2007.

* cited by examiner

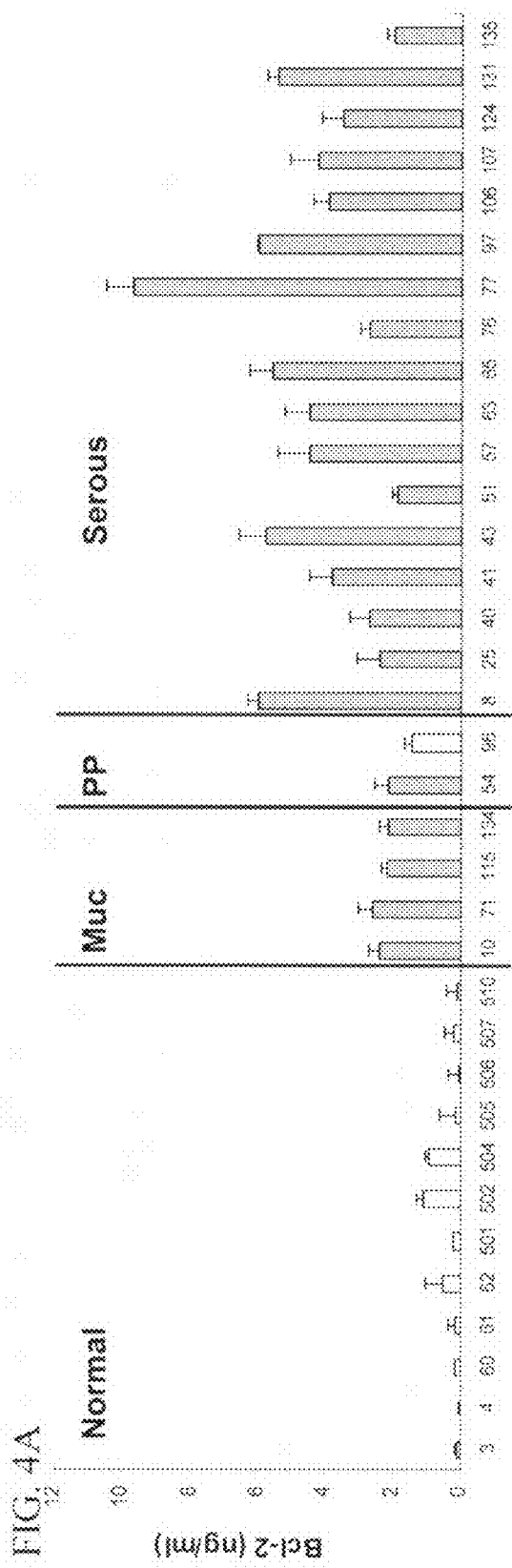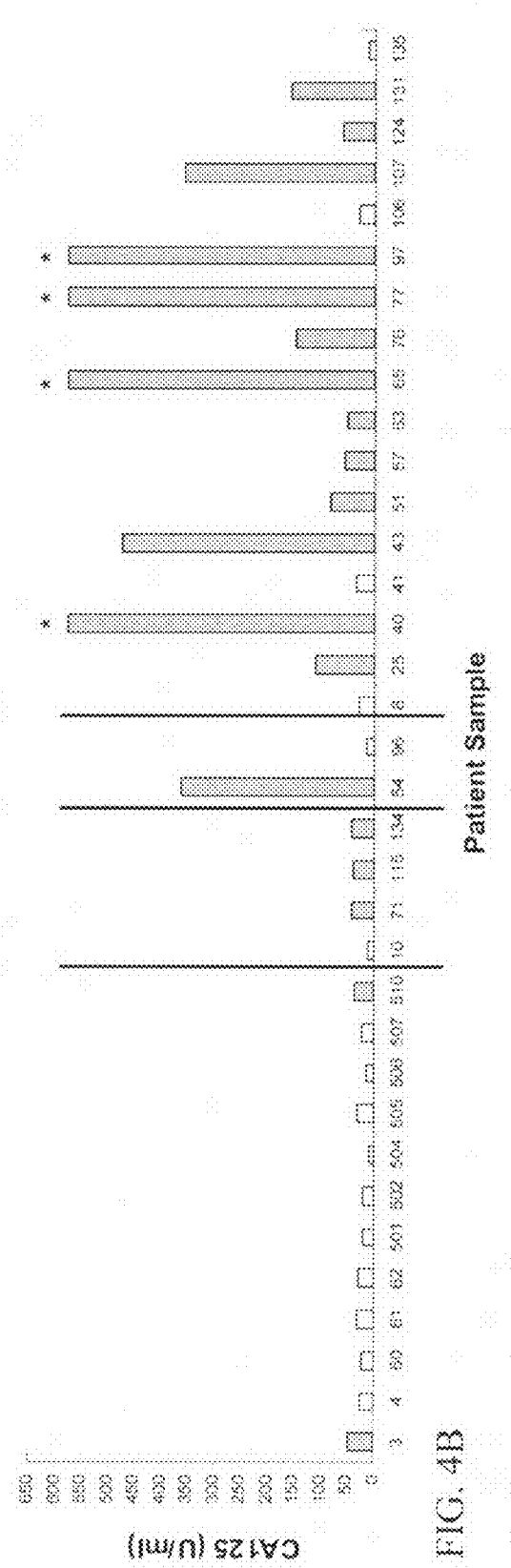

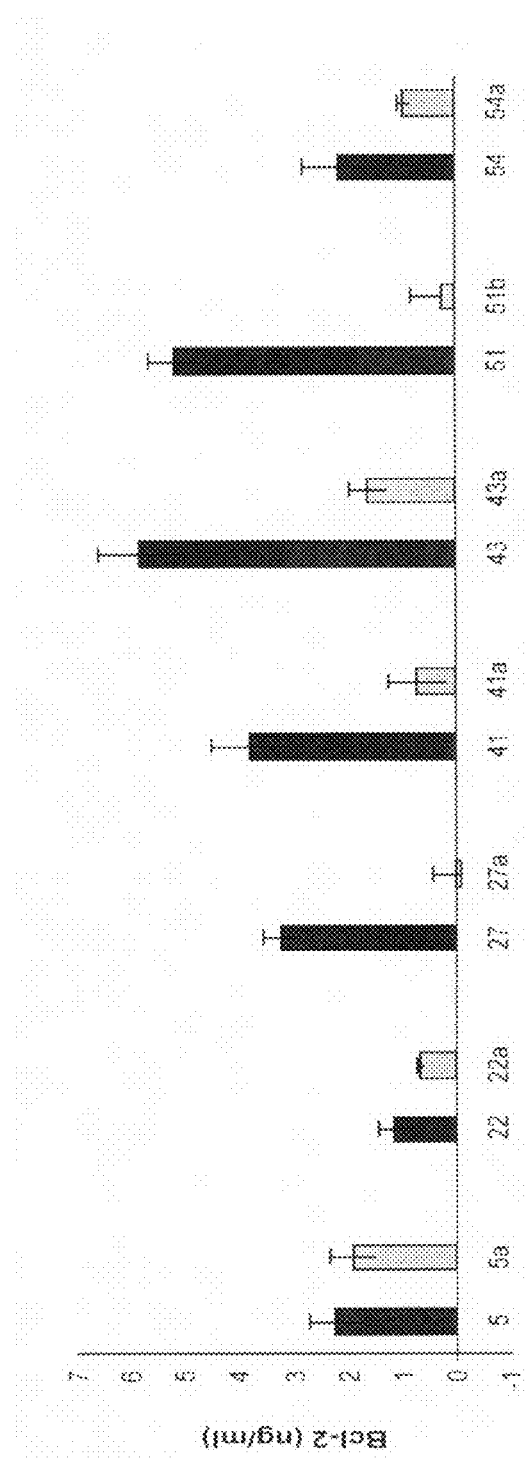
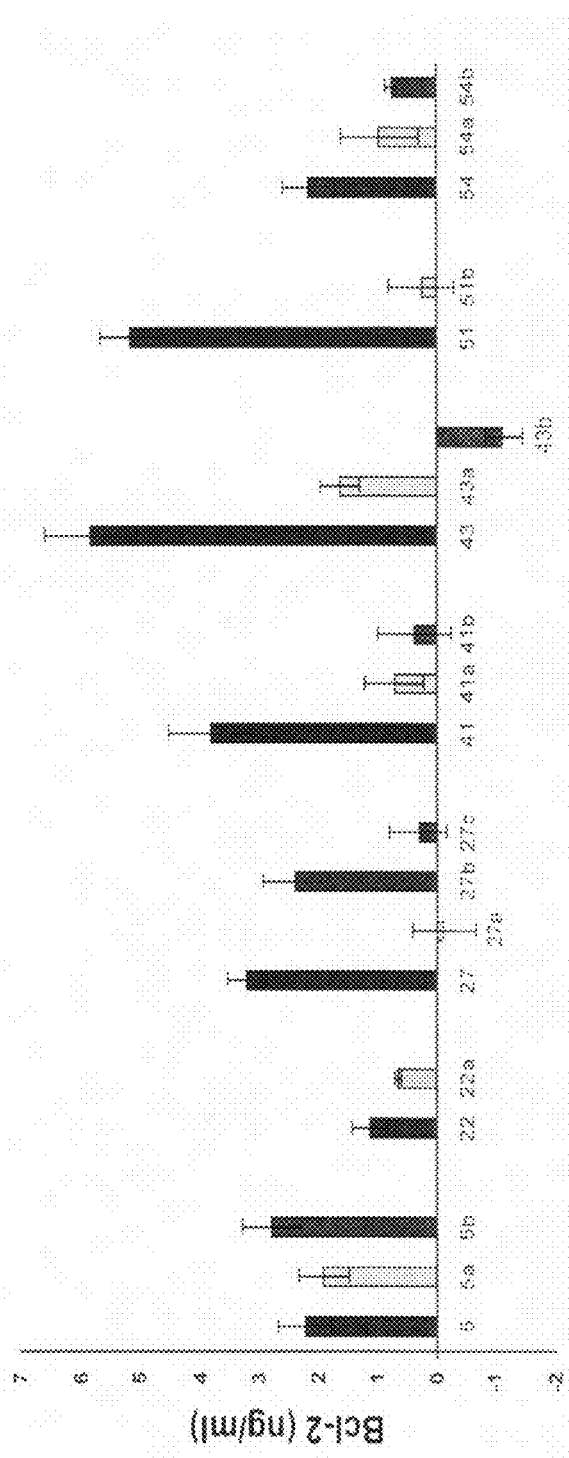
FIG. 7A
FIG. 7B

SEQUENCE LISTING

<160> NUMBER OF SEQ ID NOS: 6

<210> SEQ ID NO 1
<211> LENGTH: 6030
<212> TYPE: DNA
<213> ORGANISM: Homo sapiens
<300> PUBLICATION INFORMATION:
<301> AUTHORS: Cleary,M.L., Smith,S.D. and Sklar,J.
<302> TITLE: Cloning and structural analysis of cDNAs for bcl-2 and a
    hybrid bcl-2/immunoglobulin transcript resulting from the t(14;18)

```
           translocation
<303> JOURNAL: Cell
<304> VOLUME: 47
<305> ISSUE: 1
<306> PAGES: 19-28
<307> DATE: 1986

<400> SEQUENCE: 1
gttggccccc gttacttttc ctctgggaaa tatggcgcac gctgggagaa cagggtacga      60
taaccgggag atagtgatga agtacatcca ttataagctg tcgcagaggg gctacgagtg     120
ggatgcggga gatgtgggcg ccgcgccccc ggggccgcc cccgcgcgg gcatcttctc       180 ctcgcagccc gggcacacgc cccatacagc cgcatcccgg acccggtcg ccaggacctc      240 gccgctgcag acccggctg cccccggcgc cgccgcgggg cctgcgctca gcccggtgcc      300
acctgtggtc cacctgaccc tccgccaggc cggcgacgac ttctcccgcc gctaccgccg    360
cgacttcgcc gagatgtcca ggcagctgca cctgacgccc ttcaccgcgc ggggacgctt    420
tgccacggtg gtggaggagc tcttcaggga cggggtgaac tgggggagga ttgtggcctt    480
ctttgagttc ggtggggtca tgtgtgtgga gagcgtcaac cgggagatgt cgcccctggt    540
ggacaacatc gccctgtgga tgactgagta cctgaaccgg cacctgcaca cctggatcca    600
ggataacgga ggctgggatg cctttgtgga actgtacggc cccagcatgc ggcctctgtt    660
tgatttctcc tggctgtctc tgaagactct gctcagtttg gccctggtgg agcttgcat    720 caccctgggt gcctatctgg ccacaagtg aagtcaacat gcctgcccca acaaatatg    780 caaaaggttc actaaagcag tagaaataat atgcattgtc agtgatgttc catgaaacaa    840
agctgcaggc tgtttaagaa aaaataacac acatataaac atcacacaca cagacagaca    900
cacacacaca caacaattaa cagtcttcag gcaaaacgtc gaatcagcta tttactgcca    960
aagggaaata tcatttattt tttacattat taagaaaaaa agattttattt atttaagaca   1020 gtcccatcaa aactcctgtc tttggaaatc cgaccactaa ttgccaagca ccgcttcgtg   1080
tggctccacc tggatgttct gtgcctgtaa acatagattc gctttccatg ttgttggccg   1140
gatcaccatc tgaagagcag acggatggaa aaaggacctg atcattgggg aagctggctt   1200
tctggctgct ggaggctggg gagaaggtgt tcattcactt gcatttcttt gccctggggg   1260
ctgtgatatt aacagaggga gggttcctgt ggggggaagt ccatgcctcc ctggcctgaa   1320
gaagagactc tttgcatatg actcacatga tgcatacctg gtgggaggaa aagagttggg   1380
aacttcagat ggacctagta cccactgaga tttccacgcc gaaggacagc gatgggaaaa   1440
atgcccttaa atcataggaa agtattttt taagctacca attgtgccga gaaaagcatt    1500
ttagcaattt atacaatatc atccagtacc ttaagccctg attgtgtata ttcatatatt    1560
ttggatacgc acccccaac tcccaatact ggctctgtct gagtaagaaa cagaatcctc    1620
tggaacttga ggaagtgaac atttcggtga cttccgcatc aggaaggcta gagttaccca   1680
gagcatcagg ccgccacaag tgcctgcttt taggagaccg aagtccgcag aacctgcctg   1740
tgtcccagct tggaggcctg gtcctggaac tgagccgggg ccctcactgg cctcctccag   1800
ggatgatcaa cagggcagtg tggtctccga atgtctggaa gctgatggag ctcagaattc   1860
cactgtcaag aaagagcagt agaggggtgt ggctgggcct gtcaccctgg ggccctccag   1920
gtaggcccgt tttcacgtgg agcatgggag ccacgaccct tcttaagaca tgtatcactg   1980
tagagggaag gaacagaggc cctgggcct tcctatcaga aggacatggt gaaggctggg    2040
aacgtgagga gaggcaatgg ccacggccca ttttggctgt agcacatggc acgttggctg   2100
tgtggccttg gcccacctgt gagtttaaag caaggcttta aatgactttg gagagggtca   2160
```

```
caaatcctaa aagaagcatt gaagtgaggt gtcatggatt aattgacccc tgtctatgga    2220
attacatgta aaacattatc ttgtcactgt agtttggttt tatttgaaaa cctgacaaaa    2280
aaaaagttcc aggtgtggaa tatgggggtt atctgtacat cctggggcat aaaaaaaaaa    2340
atcaatggtg gggaactata aagaagtaac aaaagaagtg acatcttcag caaataaact    2400
aggaaatttt tttttcttcc agtttagaat cagccttgaa acattgatgg aataactctg    2460
tggcattatt gcattatata ccatttatct gtattaactt tggaatgtac tctgttcaat    2520
gtttaatgct gtggttgata tttcgaaagc tgctttaaaa aaatacatgc atctcagcgt    2580
ttttttgttt ttaattgtat ttagttatgg cctatacact atttgtgagc aaaggtgatc    2640
gttttctgtt tgagattttt atctcttgat tcttcaaaag cattctgaga aggtgagata    2700
agccctgagt ctcagctacc taagaaaaac ctggatgtca ctggccactg aggagctttg    2760
tttcaaccaa gtcatgtgca tttccacgtc aacagaattg tttattgtga cagttatatc    2820
tgttgtccct ttgaccttgt ttcttgaagg tttcctcgtc cctgggcaat tccgcattta    2880
attcatggta ttcaggatta catgcatgtt tggttaaacc catgagattc attcagttaa    2940
aaatccagat ggcaaatgac cagcagattc aaatctatgg tggtttgacc tttagagagt    3000
tgctttacgt ggcctgtttc aacacagacc cacccagagc cctcctgccc tccttccgcg    3060
ggggctttct catggctgtc cttcaggtc ttcctgaaat gcagtggtgc ttacgctcca    3120
ccaagaaagc aggaaacctg tggtatgaag ccagacctcc ccggcgggcc tcagggaaca    3180
gaatgatcag acctttgaat gattctaatt tttaagcaaa atattatttt atgaaaggtt    3240
tacattgtca aagtgatgaa tatggaatat ccaatcctgt gctgctatcc tgccaaaatc    3300
attttaatgg agtcagtttg cagtatgctc cacgtggtaa gatcctccaa gctgctttag    3360
aagtaacaat gaagaacgtg gacgctttta atataaagcc tgttttgtct tctgttgttg    3420
ttcaaacggg attcacagag tatttgaaaa atgtatatat attaagaggt cacgggggct    3480
aattgctggc tggctgccct ttgctgtggg gttttgttac ctggttttaa taacagtaaa    3540
tgtgcccagc ctcttggccc cagaactgta cagtattgtg gctgcacttg ctctaagagt    3600
agttgatgtt gcatttcct tattgttaaa aacatgttag aagcaatgaa tgtatataaa    3660
agcctcaact agtcattttt ttctcctctt cttttttttc attatatcta attattttgc    3720
agttgggcaa cagagaacca tccctatttt gtattgaaga gggattcaca tctgcatctt    3780
aactgctctt tatgaatgaa aaaacagtcc tctgtatgta ctcctcttta cactggccag    3840
ggtcagagtt aaatagagta tatgcacttt ccaaattggg gacaagggct ctaaaaaaag    3900
ccccaaaagg agaagaacat ctgagaacct cctcggccct cccagtccct cgctgcacaa    3960
atactccgca agagaggcca gaatgacagc tgacagggtc tatggccatc gggtcgtctc    4020
cgaagatttg gcaggggcag aaaactctgg caggcttaag atttggaata agtcacaga    4080 atcaaggaag cacctcaatt tagttcaaac aagacgccaa cattctctcc acagctcact    4140
tacctctctg tgttcagatg tggccttcca tttatgtgtg atctttgttt tattagtaaa    4200
tgcttatcat ctaaagatgt agctctggcc cagtgggaaa aattaggaag tgattataaa    4260
tcgagaggag ttataataat caagattaaa tgtaaataat cagggcaatc ccaacacatg    4320
tctagctttc acctccagga tctattgagt gaacagaatt gcaaatagtc tcatttgta    4380 attgaactta tcctaaaaca aatagtttat aaatgtgaac ttaaactcta attaattcca    4440
actgtacttt taaggcagtg gctgttttta gactttctta tcacttatag ttagtaatgt    4500
acacctactc tatcagagaa aaacaggaaa ggctcgaaat acaagccatt ctaaggaaat    4560
```

-continued

```
tagggagtca gttgaaattc tattctgatc ttattctgtg gtgtcttttg cagcccagac    4620
aaatgtggtt acacactttt taagaaatac aattctacat tgtcaagctt atgaaggttc    4680
caatcagatc tttattgtta ttcaatttgg atctttcagg gatttttttt ttaaattatt    4740
atgggacaaa ggacatttgt tggaggggtg ggagggagga acaattttta aatataaaac    4800
attcccaagt ttggatcagg gagttggaag ttttcagaat aaccagaact aagggtatga    4860
aggacctgta ttggggtcga tgtgatgcct ctgcgaagaa ccttgtgtga caaatgagaa    4920
acattttgaa gtttgtggta cgaccttttag attccagaga catcagcatg gctcaaagtg    4980
cagctccgtt tggcagtgca atggtataaa tttcaagctg gatatgtcta atgggtattt    5040
aaacaataaa tgtgcagttt taactaacag gatatttaat gacaaccttc tggttggtag    5100
ggacatctgt ttctaaatgt ttattatgta caatacagaa aaaaatttta taaaattaag    5160
caatgtgaaa ctgaattgga gagtgataat acaagtcctt tagtcttacc cagtgaatca    5220
ttctgttcca tgtctttgga caaccatgac cttggacaat catgaaatat gcatctcact    5280
ggatgcaaag aaaatcagat ggagcatgaa tggtactgta ccggttcatc tggactgccc    5340
cagaaaaata acttcaagca aacatcctat caacaacaag gttgttctgc ataccaagct    5400
gagcacagaa gatgggaaca ctggtggagg atggaaaggc tcgctcaatc aagaaaattc    5460
tgagactatt aataaataag actgtagtgt agatactgag taaatccatg cacctaaacc    5520
ttttggaaaa tctgccgtgg gccctccaga tagctcattt cattaagttt ttccctccaa    5580
ggtagaattt gcaagagtga cagtggattg catttctttt ggggaagctt tcttttggtg    5640
gttttgttta ttatacccttc ttaagttttc aaccaaggtt tgcttttgtt ttgagttact    5700
ggggttattt ttgttttaaa taaaaataag tgtacaataa gtgttttttgt attgaaagct    5760
tttgttatca agattttcat acttttacct tccatggctc ttttttaagat tgatacttttt    5820
aagaggtggc tgatattctg caacactgta cacataaaaa atacggtaag gatactttac    5880
atggttaagg taaagtaagt ctccagttgg ccaccattag ctataatggc actttgtttg    5940
tgttgttgga aaaagtcaca ttgccattaa actttccttg tctgtctagt taatattgtg    6000
aagaaaaata agtacagtg tgagatactg                                      6030
```

<210> SEQ ID NO 2
<211> LENGTH: 239
<212> TYPE: PRT
<213> ORGANISM: Homo sapiens

<400> SEQUENCE: 2

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Thr Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110
```

```
Ala Glu Met Ser Arg Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 3
<211> LENGTH: 6492
<212> TYPE: DNA
<213> ORGANISM: Homo sapiens
<300> PUBLICATION INFORMATION:
<301> AUTHORS: Saltman,B., Singh,B., Hedvat,C.V., Wreesmann,V.B. and
      Ghossein,R.
<302> TITLE: Patterns of expression of cell cycle/apoptosis genes along
      the spectrum of thyroid carcinoma progression
<303> JOURNAL: Surgery
<304> VOLUME: 140
<305> ISSUE: 6
<306> PAGES: 899-905
<307> DATE: 2006
<300> PUBLICATION INFORMATION:
<301> AUTHORS: Haydee Cottliar,A.S., Noriega,M.F., Narbaitz,M.,
      Rodriguez,A., Slavutsky,I.R.
<302> TITLE: Association between telomere length and BCL2 gene
      rearrangements in low- and high-grade non-Hodgkin lymphomas
<303> JOURNAL: Cancer Genet. Cytogenet.
<304> VOLUME: 171
<305> ISSUE: 1
<306> PAGES: 1-8
<307> DATE: 2006
<300> PUBLICATION INFORMATION:
<301> AUTHORS: Maluf,F.C., Cordon-Cardo,C., Verbel,D.A., Satagopan,J.M.,
      Boyle,M.G., Herr,H. Bajorin,D.F.
<302> TITLE: Assessing interactions between mdm-2, p53, and bcl-2 as
      prognostic variables in muscle-invasive bladder cancer treated
      with neo-adjuvant chemotherapy followed by locoregional surgical
<303> JOURNAL: Ann. Oncol.
<304> VOLUME: 17
<305> ISSUE: 11
<306> PAGES: 1677-1686
<307> DATE: 2006
<300> PUBLICATION INFORMATION:
<301> AUTHORS: Porebska,I., Wyrodek,E., Kosacka,M., Adamiak,J.,
      Jankowska,R., Harlozinska-Szmyrka,A.
<302> TITLE: Apoptotic markers p53, Bcl-2 and Bax in primary lung cancer
<303> JOURNAL: In Vivo
<304> VOLUME: 20
<305> ISSUE: 5
<306> PAGES: 599-604
<307> DATE: 2006

<400> SEQUENCE: 3
tttctgtgaa gcagaagtct gggaatcgat ctggaaatcc tcctaatttt tactccctct    60
ccccgcgact cctgattcat tgggaagttt caaatcagct ataactggag agtgctgaag   120
attgatggga tcgttgcctt atgcatttgt tttggtttta caaaaaggaa acttgacaga   180
ggatcatgct gtacttaaaa aatacaacat cacagaggaa gtagactgat attaacaata   240
```

```
cttactaata ataacgtgcc tcatgaaata agatccgaa aggaattgga ataaaaattt     300
cctgcatctc atgccaaggg ggaaacacca gaatcaagtg ttccgcgtga ttgaagacac    360
cccctcgtcc aagaatgcaa agcacatcca ataaaatagc tggattataa ctcctcttct    420
ttctctgggg gccgtgtgggt gggagctggg gcgagaggtg ccgttggccc ccgttgcttt   480
tcctctggga aggatggcgc acgctggagt aacagggtac gataaccggg agatagtgat   540
gaagtacatc cattataagc tgtcgcagag gggctacgag tgggatgcgg gagatgtggg    600
cgccgcgccc ccgggggccg ccccgcacc gggcatcttc tcctcccagc ccgggcacac    660
gccccatcca gccgcatccc gggacccggt cgccaggacc tcgccgctgc agaccccggc   720 tgccccggc gccgccgcgg ggcctgcgct cagcccggtg ccacctgtgg tccacctgac    780
cctccgccag gccggcgacg acttctcccg ccgctaccgc cgcgacttcg ccgagatgtc    840
cagccagctg cacctgacgc ccttcaccgc gcggggacgc tttgccacgg tggtggagga   900
gctcttcagg gacggggtga actggggag gattgtggcc ttctttgagt tcggtggggt    960
catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct    1200
gggccacaag tgaagtcaac atgcctgccc caaacaaata tgcaaaggt tcactaaagc    1260 agtagaaata atatgcattg tcagtgatgt accatgaaac aaagctgcag gctgtttaag    1320
aaaaaataac acacatataa acatcacaca cacagacaga cacacacaca cacaacaatt    1380
aacagtcttc aggcaaaacg tcgaatcagc tatttactgc caaagggaaa tatcatttat    1440 ttttacatt attaagaaaa aaagatttat ttattaaga cagtcccatc aaaactcctg     1500
tctttggaaa tccgaccact aattgccaag caccgcttcg tgtggctcca cctggatgtt    1560
ctgtgcctgt aaacatagat tcgctttcca tgttgttggc cggatcacca tctgaagagc    1620
agacggatgg aaaaaggacc tgatcattgg ggaagctggc tttctggctg ctggaggctg    1680
gggagaaggt gttcattcac ttgcatttct ttgccctggg ggctgtgata ttaacagagg    1740
gagggttcct gtggggggaa gtccatgcct ccctggcctg aagaagagac tctttgcata    1800
tgactcacat gatgcatacc tggtgggagg aaaagagttg ggaacttcag atggacctag    1860
tacccactga gatttccacg ccgaaggaca gcgatgggaa aaatgcccctt aaatcatagg    1920 aaagtatttt tttaagctac caattgtgcc gagaaaagca ttttagcaat ttatacaata    1980
tcatccagta ccttaagccc tgattgtgta tattcatata ttttggatac gcaccccca    2040 actcccaata ctggctctgt ctgagtaaga aacagaatcc tctggaactt gaggaagtga    2100
acatttcggt gacttccgca tcaggaaggc tagagttacc cagagcatca ggccgccaca    2160
agtgcctgct tttaggagac cgaagtccgc agaacctgcc tgtgtcccag cttggaggcc    2220
tggtcctgga actgagccgg ggccctcact ggcctcctcc agggatgatc aacagggcag    2280
tgtggtctcc gaatgtctgg aagctgatgg agctcagaat tccactgtca agaaagagca    2340
gtagaggggt gtggctgggc ctgtcaccct ggggcccctcc aggtaggccc gttttcacgt    2400
ggagcatggg agccacgacc cttcttaaga catgtatcac tgtagaggga aggaacagag    2460
gccctgggcc cttcctatca gaaggacatg gtgaaggctg ggaacgtgag gagaggcaat    2520
ggccacggcc cattttggct gtagcacatg gcacgttggc tgtgtggcct ggcccacct    2580 gtgagtttaa agcaaggctt taaatgactt tggagagggt cacaaatcct aaaagaagca    2640
```

```
ttgaagtgag gtgtcatgga ttaattgacc cctgtctatg gaattacatg taaaacatta    2700
tcttgtcact gtagtttggt tttatttgaa aacctgacaa aaaaaaagtt ccaggtgtgg    2760
aatatggggg ttatctgtac atcctggggc attaaaaaaa aaatcaatgg tggggaacta    2820
taaagaagta acaaaagaag tgacatcttc agcaaataaa ctaggaaatt ttttttttctt   2880 ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaaatacat gcatctcagc gttttttttgt tttttaattgt  3060 atttagttat ggcctataca ctatttgtga gcaaaggtga tcgttttctg tttgagattt    3120
ttatctcttg attcttcaaa agcattctga gaaggtgaga taagccctga gtctcagcta   3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga ccttttagaga gttgctttac gtggcctgtt   3480
tcaacacaga cccacccaga gccctcctgc cctccttccg cgggggcttt ctcatggctg    3540
tccttcaggg tcttcctgaa atgcagtggt gcttacgctc caccaagaaa gcaggaaacc    3600
tgtggtatga agccagacct ccccggcggg cctcagggaa cagaatgatc agacctttga    3660
atgattctaa ttttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt    4140
ttttctcctc ttctttttttt tcattatatc taattatttt gcagttgggc aacagagaac    4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata atcgagagg agttataata    4740 atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attagggagt cagttgaaat    5040
```

```
tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggattttt ttttaaatta ttatgggaca aaggacattt    5220
gttggagggg tgggagggag gaagaatttt taaatgtaaa acattcccaa gtttggatca    5280
gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
caatggtata aatttcaagc tggatatgtc taatgggtat ttaaacaata aatgtgcagt    5520
tttaactaac aggatatttta atgcaaccct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa ccttttggaa aatctgccgt    6000
gggccctcca gatagctcat tcattaagt ttttccctcc aaggtagaat ttgcaagagt    6060
gacagtggat tgcatttctt ttggggaagc tttcttttgg tggttttgtt tattatacct    6120
tcttaagttt tcaaccaagg tttgcttttg ttttgagtta ctggggttat ttttgtttta    6180
aataaaaata agtgtacaat aagtgttttt gtattgaaag cttttgttat caagattttc    6240 atactttac cttccatggc tctttttaag attgatactt ttaagaggtg gctgatattc    6300
tgcaacactg tacacataaa aaatacggta aggatacttt acatggttaa ggtaaagtaa    6360
gtctccagtt ggccaccatt agctataatg gcactttgtt tgtgttgttg gaaaagtca    6420 cattgccatt aaactttcct tgtctgtcta gttaatattg tgaagaaaaa taaagtacag    6480
tgtgagatac tg                                                        6492
```

<210> SEQ ID NO 4
<211> LENGTH: 239
<212> TYPE: PRT
<213> ORGANISM: Homo sapiens

<400> SEQUENCE: 4

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
```

|   | 115 |   |   |   | 120 |   |   |   | 125 |   |   |
|---|---|---|---|---|---|---|---|---|---|---|---|
| Arg | Phe | Ala | Thr | Val | Val | Glu | Glu | Leu | Phe | Arg | Asp | Gly | Val | Asn | Trp |
| 130 | | | | | 135 | | | | 140 | | |

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
210                 215                 220

Leu Val Gly Ala Cys Ile Thr Leu Gly Ala Tyr Leu Gly His Lys
225                 230                 235

```
<210> SEQ ID NO 5
<211> LENGTH: 1207
<212> TYPE: DNA
<213> ORGANISM: Homo sapiens

<400> SEQUENCE: 5
tttctgtgaa gcagaagtct gggaatcgat ctggaaatcc tcctaatttt tactccctct      60
ccccgcgact cctgattcat tgggaagttt caaatcagct ataactggag agtgctgaag     120
attgatggga tcgttgcctt atgcatttgt tttggtttta caaaaaggaa acttgacaga     180
ggatcatgct gtacttaaaa aatacaacat cacagaggaa gtagactgat attaacaata     240
cttactaata ataacgtgcc tcatgaaata aagatccgaa aggaattgga ataaaaattt     300
cctgcatctc atgccaaggg ggaaacacca gaatcaagtg ttccgcgtga ttgaagacac     360
ccctcgtcc aagaatgcaa agcacatcca ataaaatagc tggattataa ctcctcttct     420
ttctctgggg gccgtggggt gggagctggg gcgagaggtg ccgttggccc ccgttgcttt     480
tcctctggga aggatggcgc acgctggag aacagggtac gataaccggg agatagtgat     540
gaagtacatc cattataagc tgtcgcagag gggctacgag tgggatgcgg gagatgtggg     600
cgccgcgccc ccgggggccg ccccgcacc gggcatcttc tcctcccagc ccggcacac      660
gccccatcca gccgcatccc gggacccggt cgccaggacc tcgccgctgc agaccccggc     720
tgccccggc gccgccgcgg ggcctgcgct cagcccggtg ccacctgtgg tccacctgac      780
cctccgccag gccggcgacg acttctcccg ccgctaccgc cgcgacttcg ccgagatgtc     840
cagccagctg cacctgacgc ccttcaccgc gcggggacgc tttgccacgg tggtggagga     900
gctcttcagg gacggggtga actggggag gattgtggcc ttctttgagt tcggtggggt     960
catgtgtgtg gagagcgtca accgggagat gtcgcccctg gtggacaaca tcgccctgtg    1020
gatgactgag tacctgaacc ggcacctgca cacctggatc caggataacg gaggctgggt    1080
aggtgcactt ggtgatgtga gtctgggctg aggccacagg tccgagatgc ggggggttgga    1140
gtgcggggtgg gctcctgggg caatgggagg ctgtggagcc ggcgaaataa aatcagagtt    1200
gttgcta                                                              1207

<210> SEQ ID NO 6
<211> LENGTH: 205
<212> TYPE: PRT
<213> ORGANISM: Homo sapiens

<400> SEQUENCE: 6
```

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35              40              45

Phe Ser Ser Gln Pro Gly His Thr Pro His Pro Ala Ala Ser Arg Asp
        50              55              60

Pro Val Ala Arg Thr Ser Pro Leu Gln Thr Pro Ala Ala Pro Gly Ala
65              70                  75                  80

Ala Ala Gly Pro Ala Leu Ser Pro Val Pro Pro Val Val His Leu Thr
                85              90                  95

Leu Arg Gln Ala Gly Asp Asp Phe Ser Arg Arg Tyr Arg Arg Asp Phe
                100             105                 110

Ala Glu Met Ser Ser Gln Leu His Leu Thr Pro Phe Thr Ala Arg Gly
            115             120                 125

Arg Phe Ala Thr Val Val Glu Glu Leu Phe Arg Asp Gly Val Asn Trp
        130             135                 140

Gly Arg Ile Val Ala Phe Phe Glu Phe Gly Gly Val Met Cys Val Glu
145             150                 155                 160

Ser Val Asn Arg Glu Met Ser Pro Leu Val Asp Asn Ile Ala Leu Trp
                165             170                 175

Met Thr Glu Tyr Leu Asn Arg His Leu His Thr Trp Ile Gln Asp Asn
                180             185                 190

Gly Gly Trp Val Gly Ala Leu Gly Asp Val Ser Leu Gly
        195             200                 205
```

DETECTION OF CANCER BY ELEVATED LEVELS OF BCL-2

CROSS-REFERENCE TO RELATED APPLICATION

The present application claims the benefit of U.S. Provisional Application Ser. No. 60/771,677, filed Feb. 9, 2006, which is hereby incorporated by reference herein in its entirety, including any figures, tables, nucleic acid sequences, amino acid sequences, and drawings.

This invention was made with government support under US Army Department of Defense New Idea Award #W81XWH-07-1-0276(PAK). The government has certain rights in the invention.

BACKGROUND OF THE INVENTION

Cancer markers are substances that can be found in the body (usually in the blood or urine) when cancer is present. They can be products of the cancer cells themselves, or of the body in response to cancer or other conditions. For several reasons, cancer markers themselves are usually not enough to diagnose (or rule out) a specific type of cancer. Most cancer markers can be produced by normal cells as well as by cancer cells, even if in smaller amounts. Sometimes, non-cancerous diseases can also cause levels of certain cancer markers to be higher than normal. Further, not every person with cancer may have higher levels of a cancer marker. For these reasons, only a small amount of cancer markers are commonly used by most doctors. When a doctor does look at the level of a certain cancer marker, he or she will typically consider it along with the results of the patient's history and physical exam, and other lab tests or imaging tests.

Screening refers to looking for cancer in individuals who have no symptoms of the disease, while early detection is finding cancer at an early stage of the disease, when it is less likely to have spread (and is more likely to be treated effectively). Although cancer markers were originally investigated and developed to test for cancer in people without symptoms, very few markers have been shown to be helpful in this way.

Ovarian cancer has the highest mortality among gynecological cancers. The lack of early symptoms and the absence of a reliable screening test to detect ovarian cancer result in over 70% of women being diagnosed after the disease has spread beyond the ovary so that the prognosis is poor with approximately 12,000 deaths due to ovarian cancer annually (5-year survival is no better than 37%). Currently, physical pelvic examination by a physician, ultrasound or measuring blood levels for CA125 are the only standard methods available for detection of ovarian cancer. However, none of these methods provides a reliably consistent and accurate method to detect ovarian cancer. For example, while over 80% of women with ovarian cancer will have elevated blood levels of CA125, blood levels of CA125 are only about 50% accurate for detecting early stage disease. The development of an alternate and new test to reliably and accurately detect all ovarian cancers is imperative. Thus, what is needed is a technology that overcomes the current lack of a reliable, accurate, safe and cost-effective test for ovarian cancer. Furthermore, what is needed is a technology that accurately detects all ovarian cancers, many of which now go undetected, as well as monitor disease burden throughout the course of ovarian cancer.

An accurate, safe, simple, and reliable test to diagnosis ovarian cancer would benefit all women, in the United States and worldwide, including medically underserved geographical areas and especially women at high risk for developing ovarian cancer. Given that approximately 25,000 women are diagnosed with ovarian cancer annually in the U.S., a biomarker of ovarian cancer that is detectable in both early and late stages of disease would not only confirm the diagnosis of ovarian cancer, but could also potentially detect thousands of previously undiagnosed ovarian cancers. This is especially important for detection of ovarian cancer in early stages where the disease is confined to the ovary, but currently accounts for less than 10% of diagnosed ovarian cancers. In these situations, surgical debulking of the diseased ovary increases patient survival to over 90% and would be expected to reduce medical costs. The ability to accurately detect and monitor ovarian cancer in each patient through the course of her disease, would not only serve for initial ovarian cancer diagnosis, but would also indicate therapeutic efficacy and/or recurrent disease. The development of a commercially available, FDA-approved ELISA-based test, for example, could become the gold standard for clinical diagnosis of ovarian cancer.

While apoptosis is an essential biological process for normal development and maintenance of tissue homeostasis, it is also involved in a number of pathologic conditions including tissue injury, degenerative diseases, immunological diseases and cancer (Lowe, S. W. and Lin, A. W. *Carcinogenesis*, 2000, 21:485-495). Whether activated by membrane bound death receptors (Ashkenazi, A. et al. *J. Clin. Invest.*, 1999, 104:155-162; Walczak, H. Krammer, P. H. *Exp. Cell Res*, 2000, 256: 58-66) or by stress-induced mitochondrial perturbation with subsequent cytochrome c release (Loeffler, M. and Kroemer, G. *Exp. Cell Res.*, 2000, 256:19-26; Wernig, F. and Xu, Q. *Prog. Biophys. Mol. Biol.*, 2002, 78:105-137; Takano, T. et al. *Antiox. Redox. Signal*, 2002, 4:533-541), activation of downstream caspases leads to stepwise cellular destruction by disrupting the cytoskeleton, shutting down DNA replication and repair, degrading chromosomal DNA, and, finally, disintegrating the cell into apoptotic bodies (Nagata, S. *Exp. Cell Res.*, 2000, 256:12-18). The key regulators of apoptosis include members of the bcl-2 protein family (Farrow, S. N. and Brown, R. *Curr. Opin. Gen. Dev.*, 1996, 6:45-49).

The bcl-2 protein family consists of both pro- and anti-apoptotic protein family members that act at different levels of the apoptotic cascade to regulate apoptosis. The bcl-2 family members contain at least one Bcl-2-homology (BH) domain (Farrow, S. N. and Brown, R. *Curr. Opin. Gen. Dev.*, 1996, 6:45-49). Though all bcl-2 family members demonstrate membrane channel forming activity, Bcl-2 (the archetypal bcl-2 family member) channels are cation ($Ca^{++}$) selective and, owing to its exclusive ER and mitochondrial membrane localization (Thomenius, M. J. and Distelhorst, C. W. *J. Cell Sci.*, 2003, 116:4493-4499), the anti-apoptotic function of Bcl-2 is at least partly mediated by its ability to prevent calcium release from the ER and subsequent mitochondrial membrane perturbation and cytochrome c release. Since Bcl-2 is overexpressed in many tumor types including ovarian cancer (Sharma, H. et al. *Head Neck*, 2004, 26:733-740; Hanaoka, T. et al. *Intl. J. Clin. Oncol.*, 2002, 7:152-158; Trisciuoglio, D. et al. *J. Cell Physiol.*, 2005, 205:414-421; Khalifeh, I. et al. *Int. J. Gynecol. Pathol.*, 2004, 23:162-169; O'Neill, C. J. et al. *Am. J. Surg. Pathol.;* 2005, 29:1034-1041), it contributes to chemoresistance by stabilizing the mitochondrial membrane against apoptotic insults. Currently, preclinical studies focus on the development of agents to inhibit Bcl-2, including antisense oligonucleotides such as G3,139 (Ackermann, E. J. et al. *J. Biol. Chem.*, 1999, 274: 11245-11252), and small molecular inhibitors of Bcl-2 (Lickliter, J. D. et al. *Leukemia*, 2003, 17:2074-2080). Though such studies target Bcl-2 for therapeutic intervention, quantification of urinary Bcl-2 has not previously been reported in the literature.

It would be advantageous to have available assays that provide safe, sensitive, specific, and economical methods for the detection of cancers such as ovarian cancer, which would benefit society worldwide.

BRIEF SUMMARY OF THE INVENTION

The present invention relates to cancer screening. Bcl-2 constitutes a biomarker for prognosis, diagnosis, and monitoring of cancer, such as reproductive cancer. For example, Bcl-2 may be used to diagnose and monitor early stage and late stage ovarian cancer. Bcl-2 may be used as a biomarker for cancer before surgery and after relapse. Bcl-2, and agents that bind Bcl-2 polynucleotides or polypeptides may be used to detect and monitor ovarian cancer, and other reproductive or non-reproductive cancers.

Thus, more particularly, this invention relates to the detection of cancer by screening for elevated levels of Bcl-2 in biological samples, such as urine, blood (e.g., whole blood, serum, or plasma), and ascites fluid. In one embodiment, the cancer is ovarian cancer. In another embodiment, the cancer is a type selected from the group consisting of breast, endometrial, cervical, lung, colon, prostate, melanoma, glioblastoma, sarcoma, bladder, and head and neck. Optionally, the method further comprises verifying that the subject is suffering from the cancer detected (e.g., by assessing for the presence of one or more cancer symptoms, detecting additional cancer markers, detecting the presence of the cancer through an imaging modality such as X-ray, CT, nuclear imaging (PET and SPECT), ultrasound, MRI) and/or treating the subject for the cancer detected (e.g., by surgery, chemotherapy, and/or radiation).

The invention also relates to kits for carrying out the methods of the invention.

In another aspect, the present invention relates to a device for the rapid detection of Bcl-2 in a bodily fluid such as blood or urine. Preferably, the device is a lateral flow device. In one embodiment, the device comprises an application zone for receiving a sample of bodily fluid such as blood or urine; a labeling zone containing a binding agent that binds to Bcl-2 in the sample; and a detection zone where Bcl-2-bound binding agent is retained to give a signal, wherein the signal given for a sample from a subject with a Bcl-2 level lower than a threshold concentration is different from the signal given for a sample from a patient with a Bcl-2 level equal to or greater than a threshold concentration.

In another aspect, the invention relates to a simple, rapid, reliable, accurate and cost effective test for Bcl-2 in a bodily fluid such as blood or urine, similar to currently available in-home pregnancy tests that could be used by subjects at home, in a physicians' office, or at a patient's bedside.

In one embodiment, the test is a method for measuring Bcl-2 in a bodily fluid, comprising: (a) obtaining a sample of bodily fluid, such as blood or urine, from a subject; (b) contacting the sample with a binding agent that binds to any Bcl-2 in the sample; (c) separating Bcl-2-bound binding agent; (d) detecting a signal associated with the separated binding agent from (c); and (e) comparing the signal detected in step (d) with a reference signal which corresponds to the signal given by a sample from a subject with a Bcl-2 level equal to a threshold concentration. In one embodiment, the bodily fluid is urine, and the threshold concentration is between 0 ng/ml and 2.0 ng/ml. In another embodiment, the bodily fluid is urine, and the threshold concentration is 1.8 ng/ml.

To assess whether urinary levels of Bcl-2 could be used to detect ovarian cancer, urine was collected from normal healthy volunteers, from patients with ovarian cancer and measured for Bcl-2 by ELISA. The average amount of Bcl-2 in the urine of cancer patients was generally at least 10× greater than healthy controls. In addition, none of the urine samples collected from 35 women with benign gynecologic disease (including teratomas, ovarian cysts, leiomyomas, polycystic ovarian disease, adenofibromas or cystadenomas) had Bcl-2 levels above that found in normal, healthy volunteers. Urinary levels of Bcl-2 decreased up to 100% in ovarian cancer patients following debulking surgery. The sensitivity and specificity for elevated urinary Bcl-2 associated with ovarian cancer was almost 100% while blood levels of CA125>35 U/ml only identified 68% of ovarian cancer patients. Comparison of clinical parameters indicated that urinary levels of Bcl-2 correlated well with tumor stage and grade. However, urinary levels of Bcl-2 were not related to patient age or tumor size. Therefore, quantification of urinary Bcl-2 by ELISA-based assays provides a safe, sensitive, specific and economical method to detect ovarian cancer, to monitor ovarian cancer throughout the course of disease and to predict therapeutic and prognostic outcome.

3A illustrates that urinary levels of Bcl-2 were lowest in stage I and II tumors (average ng/ml Bcl-2=2.2) where the disease is localized within the ovary and peritoneal cavity, respectively. Urinary levels of Bcl-2 were greatest among stage III and V (average ng/ml Bcl-2=4.22) when the disease has spread well beyond the ovary or is recurrent disease, respectively.

FIGS. 4A and 4B are a pair of histograms depicting the ability of urinary Bcl-2 (FIG. 4A) relative to the measurements of plasma levels of CA125 (FIG. 4B) in detecting ovarian cancer. Wherever possible, levels of urinary Bcl-2 as previously shown in FIGS. 1-3 were compared with plasma levels of CA125 from the same normal healthy volunteers and cancer patients. The latter group included patients with mucinous ovarian cancer (Muc), primary peritoneal cancer (PP) and serous ovarian cancer (Serous). CA125 levels were determined by ELISA (kits from Bio-Quant, San Diego, Calif., Catalog #BQ1013T) in triplicate. The data are expressed as the average ng/ml Bcl-2 (A) and average U/ml CA125 (FIG. 4B). The sensitivity and specificity to detect ovarian cancer by elevated levels of urinary Bcl-2 was almost 100%. In contrast, CA125 blood levels>35 U/ml, the current standard for ovarian cancer detection, only correctly identified 68% of ovarian cancer patients.

Figure 5:
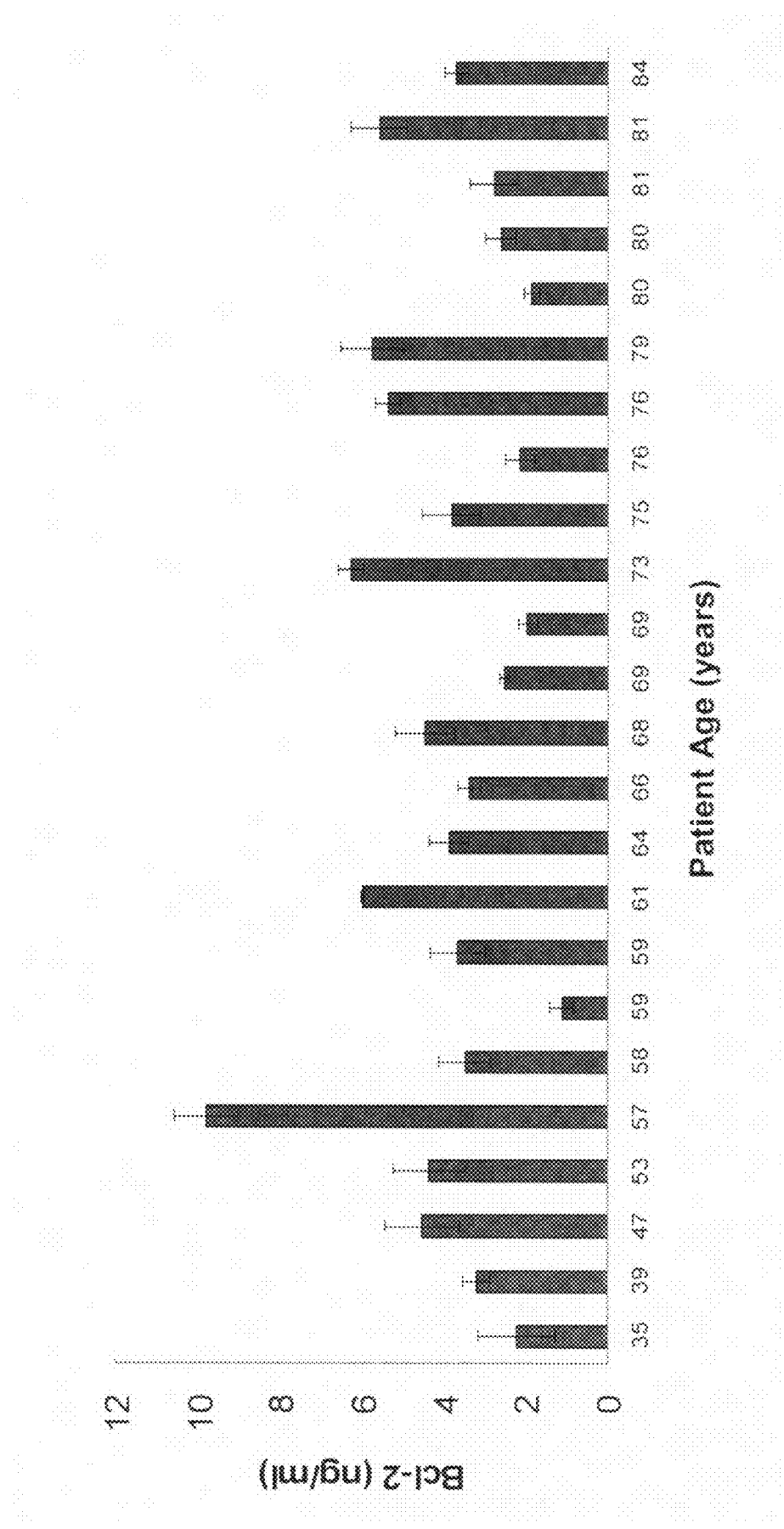

FIG. 5 is a histogram showing that urinary Bcl-2 does not correlate with patient age. To examine whether elevated urinary levels of Bcl-2 in cancer patients correlated with patient age, levels of urinary Bcl-2 (as determined previously in FIGS. 1-3 and 4A-4B) were compared against patient age in years. Though the average age of normal healthy volunteers in this study was somewhat lower (54.8 years) than cancer patients (66.2 years), there was no statistical difference in age between the groups due to the wide range in age (see insert in FIG. 5). In addition, the average age of cancer patients is in agreement with the literature and clinical data indicating that ovarian cancer generally targets peri- and post-menopausal women. However, there did not appear to be a correlation between urinary levels of Bcl-2 with patient age.

Figure 6:
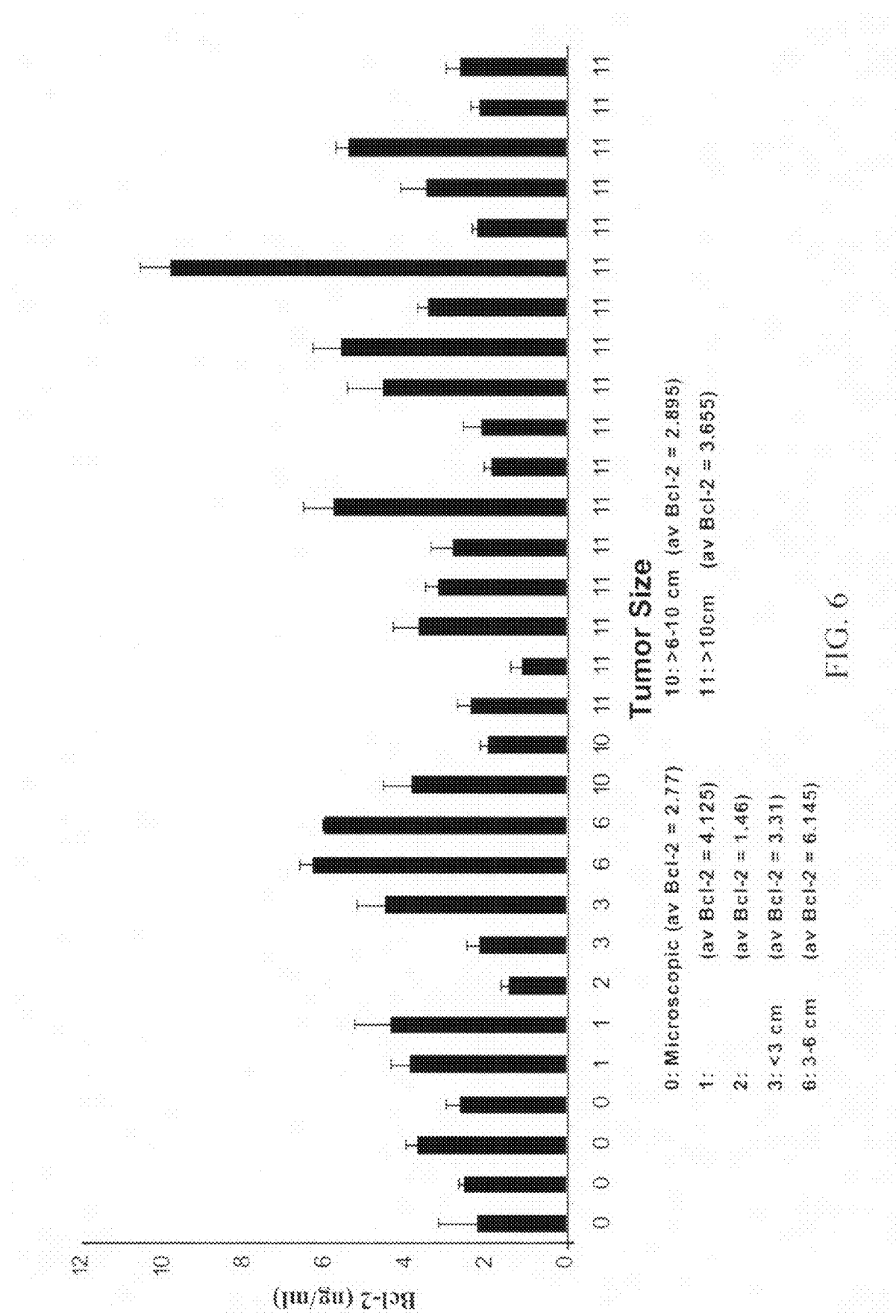

FIG. 6 is a histogram showing that urinary Bcl-2 does not correlate with ovarian tumor size. To examine whether elevated urinary levels of Bcl-2 in cancer patients correlated with tumor size, levels of urinary Bcl-2 (as determined previously in FIGS. 1-3 and 4A-4B) were compared against tumor size. Tumors were grouped as: 1=microscopic in size; 3=tumors less than 3 cm; 6=tumors between 3 and 6 cm; 10=tumors greater than 6 cm and up to 10 cm; 11=tumors greater than 10 cm. The data indicate that there did not appear to be a correlation between urinary levels of Bcl-2 with tumor size.

FIGS. 7A and 7B are a pair of histograms showing that urinary Bcl-2 decreases after ovarian cancer debulking surgery. To further test the accuracy of urinary Bcl-2 to detect ovarian cancer, levels of urinary Bcl-2 were compared in those available ovarian cancer patients immediately prior to (black bars) and within 2 weeks following (grey bars) initial debulking surgery (removal of all visible tumor) (FIG. 7A). For those 7 patients where urine samples were collected before and after initial surgery, Bcl-2 levels decreased up to 100% following surgical removal of tumor. These data, then, suggest that the tumor is the source of Bcl-2 found elevated in the urine of patients with ovarian cancer and that levels of urinary Bcl-2 parallel the presence of ovarian cancer. In addition, urine samples were collected from 5 of the 7 patients in FIG. 7A on subsequent follow up clinical visits ranging from 7 to 11 months following initial surgery and measured for Bcl-2 (blue bars) (FIG. 7B). Urinary Bcl-2 levels remained low in 3 follow-up patients (#41, 43, 54) and became elevated in 2 patients (#5, 27). Preliminary chart review indicated that patients #41, 43, 54 were undergoing chemotherapy at the time of follow-up visits and that their ovarian cancer disease was under control. In contrast, chart review suggests that patients #5, 27 had recurrent disease (5B, 27B) and that patient #27b underwent additional tumor debulking surgery. In agreement with the clinical information, urinary Bcl-2 levels remained reduced in patients undergoing chemotherapy and who had no apparent or minimal residual disease (#41, 43, 54). Likewise, elevated urinary Bcl-2 levels correlated with the presence of recurrent disease (#5b, 27B) and decreased with subsequent disease debulking (#27c).

Figure 8A:
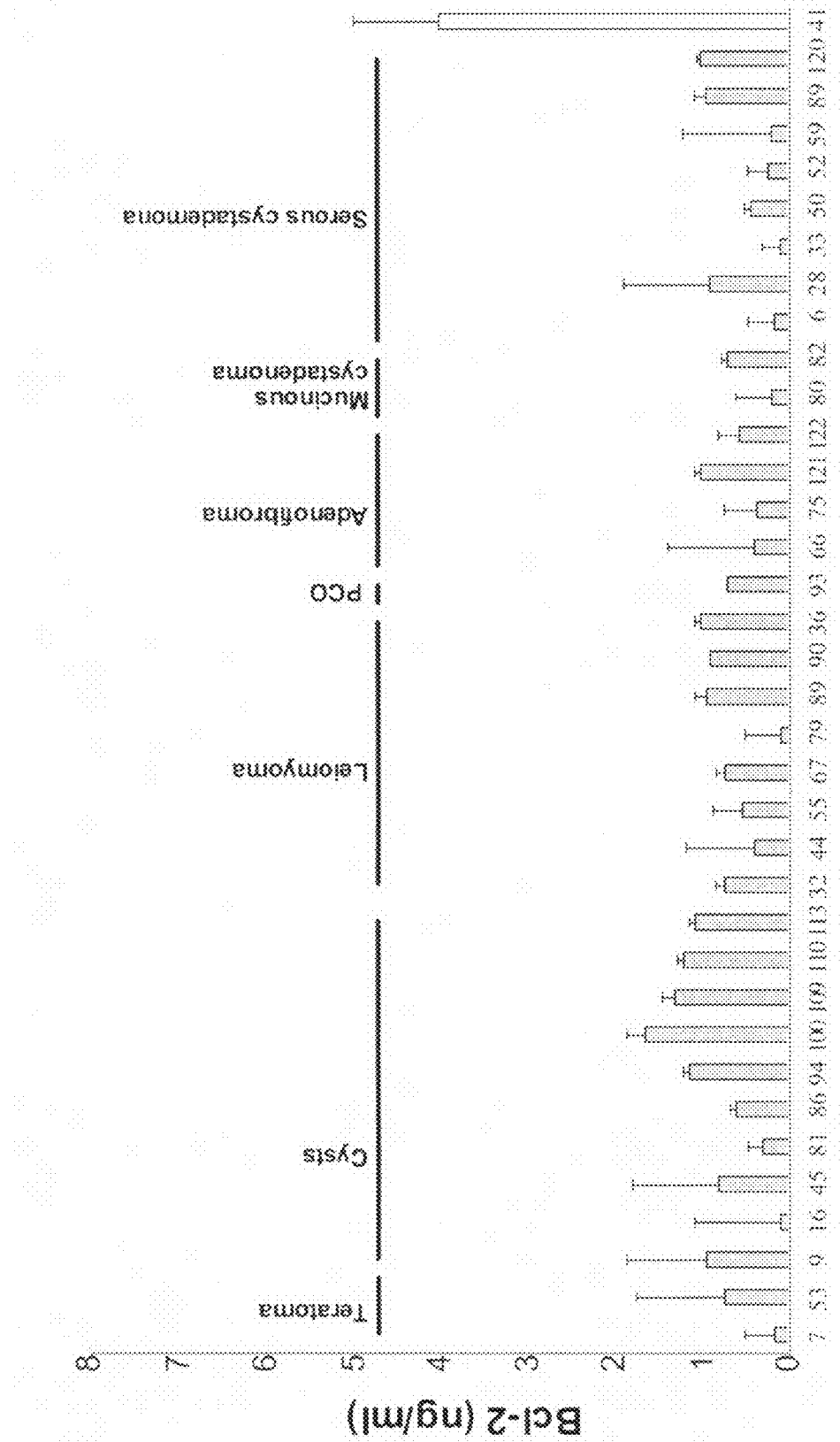
Figure 8B:
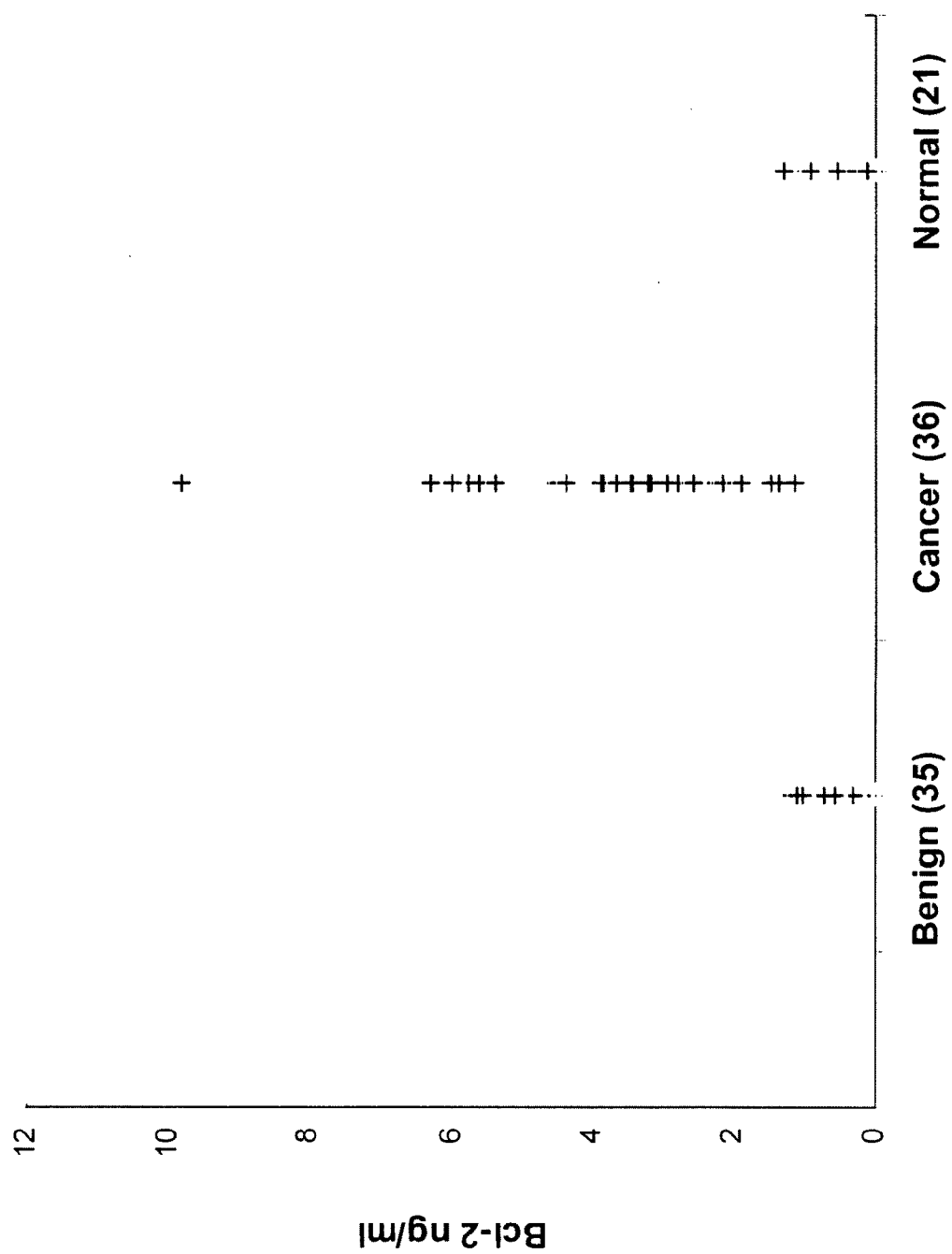

FIGS. 8A and 8B show results of Bcl-2 testing in patients with benign gynecologic disease. Urinary samples were examined by ELISA for Bcl-2 in patients with benign gynecologic disease. Samples were examined in triplicate and the data expressed as the average ng/ml of Bcl-2±S.E (FIG. 8A). Benign gynecologic disease samples were subdivided by type (benign cystic teratoma, simple cyst, leiomyoma, polycystic ovary, adenofibroma, mucinous and serous cystadenoma) with ovarian cancer patient sample #41 (white bar) serving as an internal positive control. Average urinary Bcl-2 ng/ml±S.E. among benign disease are indicted below their respective heading. Samples from FIG. 2 and FIG. 3A were re-plotted to show distribution of Bcl-2 expression for this study group (n=92), shown in FIG. 8B. Bcl-2 levels in benign, cancer and normal individuals ranged from 0.115-1.016 ng/ml, 1.12-9.8 ng/ml and 0-1.26 ng/ml and averaged 0.614 ng/ml, 3.4 ng/ml and 0.21 ng/ml, respectively.

Figure 9:
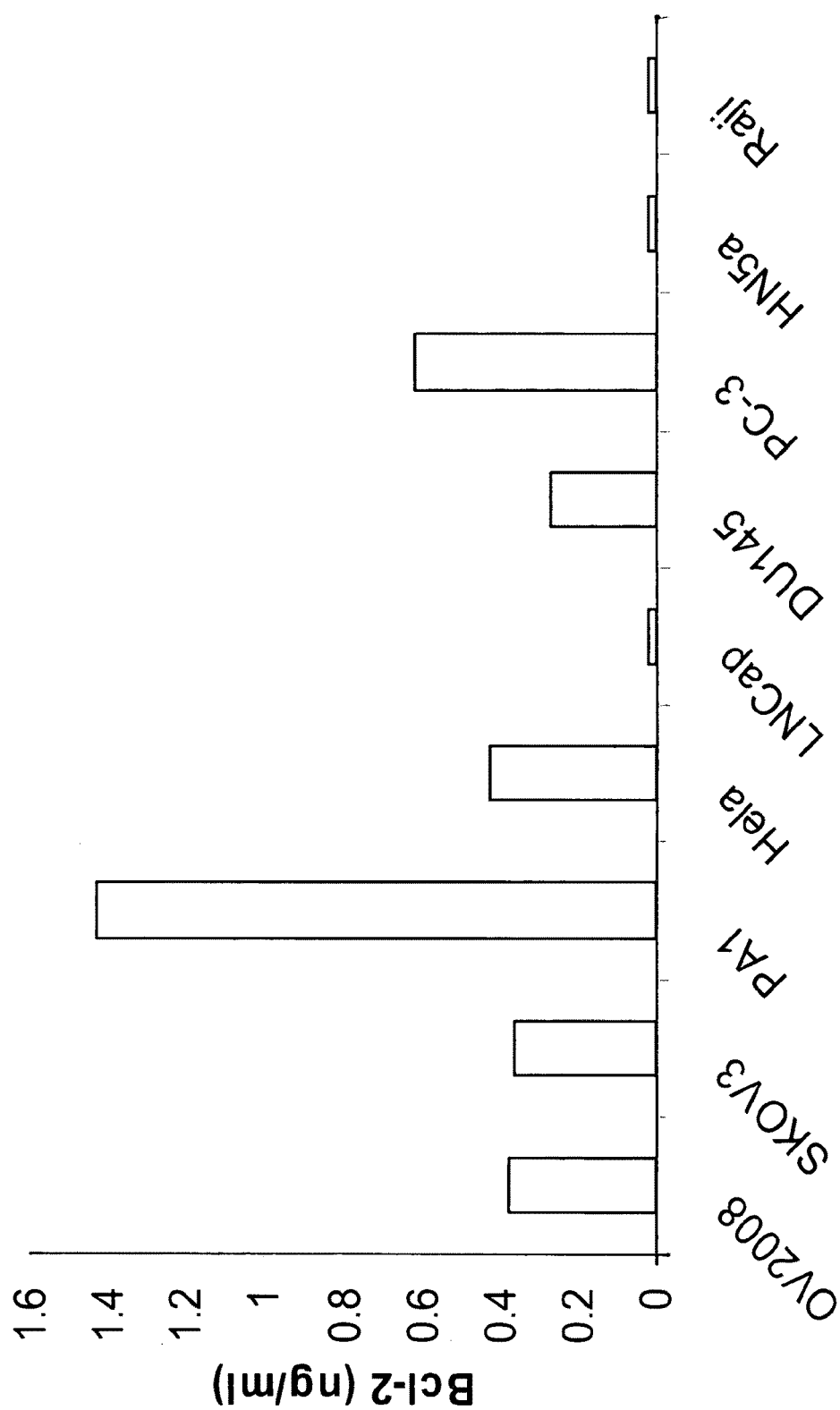

FIG. 9 is a histogram showing that Bcl-2 can be secreted into cell culture conditioned medium. Conditioned medium (CM) was collected from established cancer cell lines representing ovarian (OV2008, SKOV3, PA1), cervical (Hela), prostate (LNCap, DU145, PC-3), head and neck (HN5a) and lymphoma (Raji) cancers and examined by ELISA for presence of Bcl-2. Data are expressed as the mean of triplicate samples. The presence of Bcl-2 in the CM of ovarian, cervical and prostate cancer cell cultures suggests that these cancer cells produce and secrete Bcl-2.

Figure 10:
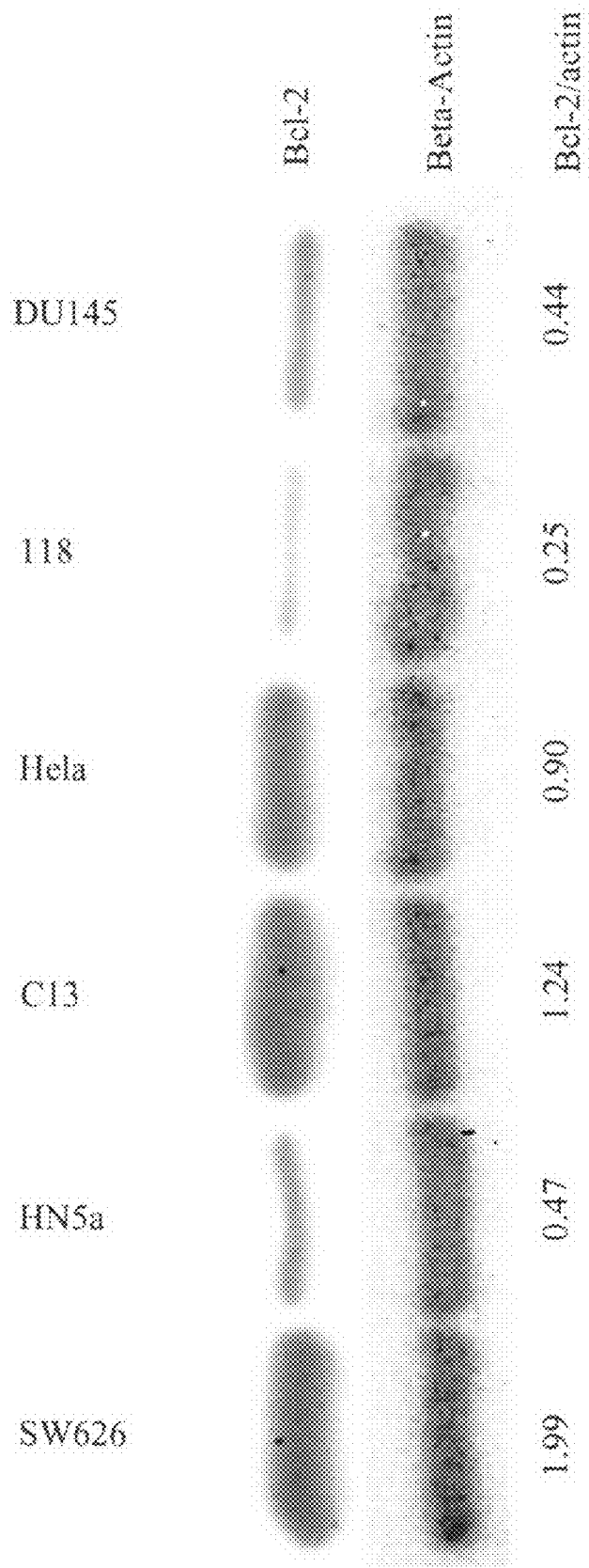

FIG. 10 shows that Bcl-2 is over-expressed in some cancers cells. Cell lysates from established cancer cell lines representing ovarian (SW626, C13), head and neck (HN5a), cervical (Hela) and prostate (DU145) cancers were western immunoblotted for Bcl-2. Actin served as a loading control and FHI-OSE118 cells (SV-40 large T antigen transfected human ovarian surface epithelial cells) served as a normal, non-malignant ovarian surface epithelial control cells. Following densitometric analyses, the level of Bcl-2 was normalized to actin, noted below the blots. Normal cells contained negligible amounts of bcl-2 while ovarian and cervical cancer cells contained the greatest amount of Bcl-2.

Figure 11:
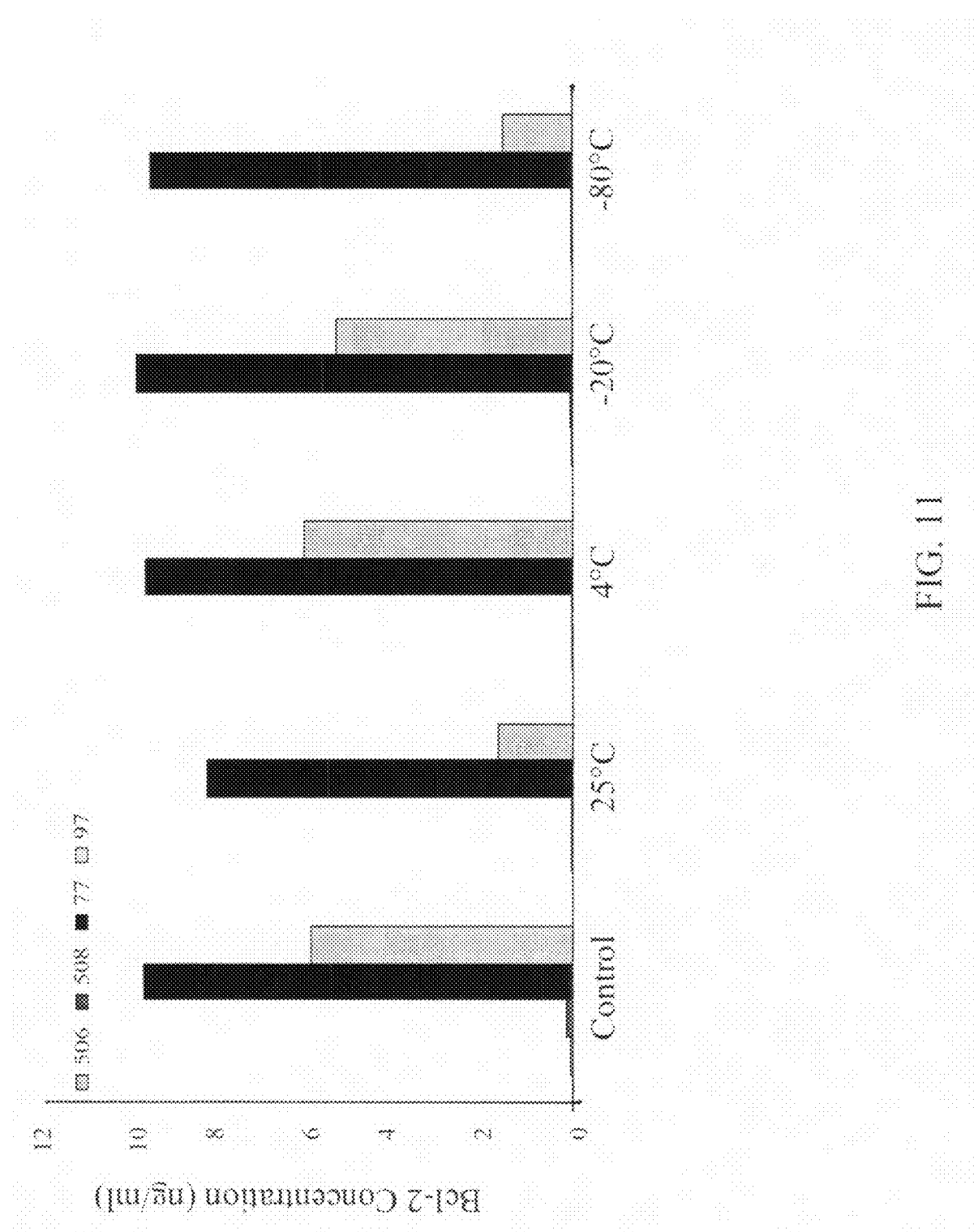

FIG. 11 shows Bcl-2 protein concentrations following storage. Urine samples from normal healthy individuals (#506, 508) and patients with ovarian cancer (#77, 97) were originally tested for Bcl-2 as part of this study (control) and following storage for 4 days at either room temperature (25° C.), in a fridge (4° C.), in a −20° C. freezer (−20° C.) or in a −80° C. freezer (−80° C.). All samples were tested in duplicate for urinary levels of Bcl-2 using an ELISA kit (BenderMed Systems).

Figure 12:
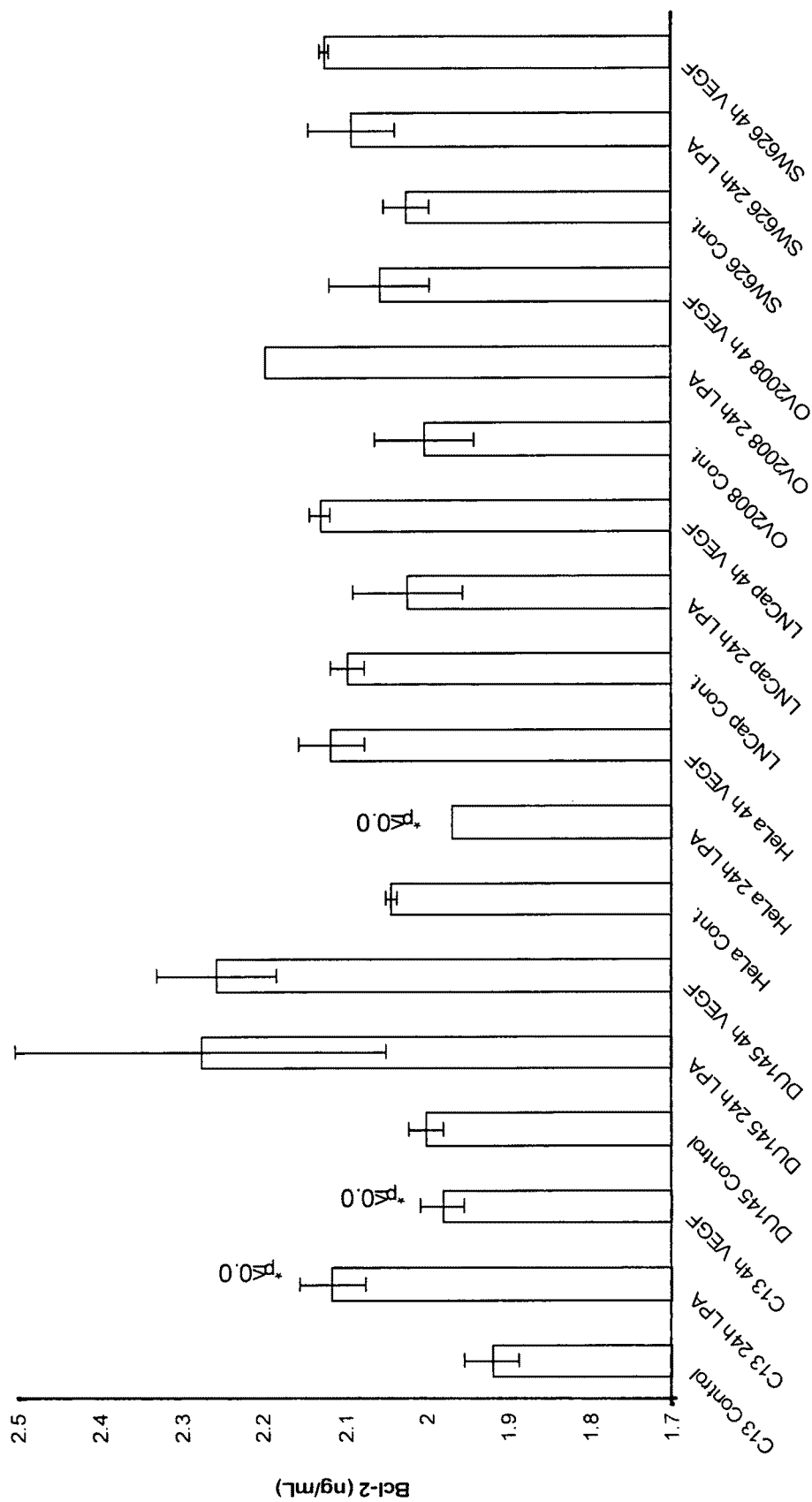

FIG. 12 shows Bcl-2 protein concentrations in conditioned medium (CM) of cancer cell lines following treatment with lysophosphatidic acid (LPA), including DU145, a prostate cancer cell line. The figure shows that treatment with LPA, which often feeds back into cancer cells in the manner of an autocrine loop, stimulates secretion of Bcl-2 into the CM of some cancer cell types. As these cancer cell lines secrete Bcl-2 into their CM, as do ovarian cancer cell lines, the in vivo tumor counterparts of such cell lines potentially secrete Bcl-2 into biological fluids such as urine and/or blood and may be detected using the present invention.

BRIEF DESCRIPTION OF THE SEQUENCES

SEQ ID NO:1 is human Bcl-2 DNA (GenBank accession no. M14745); coding region (CDS): bases 32-751.

SEQ ID NO:2 is human Bcl-2 protein (GenBank accession no. AAA35591).

SEQ ID NO:3 is human Bcl-2 DNA, transcript variant alpha (GenBank accession no. NM_000633); CDS: bases 494-1213.

SEQ ID NO:4 is human Bcl-2 protein, transcript variant alpha (GenBank accession no. NP_000624).

SEQ ID NO:5 is human Bcl-2 DNA, transcript variant beta (GenBank accession no. NM_000657); CDS: bases 494-1111.

SEQ ID NO:6 is human Bcl-2 protein, transcript variant beta (GenBank accession no. NP_000648).

DETAILED DESCRIPTION OF THE INVENTION

Bcl-2 is an effective molecular marker for cancer such as ovarian cancer. Cancer markers (also called tumor markers) are molecules such as hormones, enzymes, and immunoglobulins found in the body that are associated with cancer and whose measurement or identification is useful in patient diagnosis or clinical management. They can be products of the cancer cells themselves, or of the body in response to cancer or other conditions. Most cancer markers are proteins. Some cancer markers are seen only in a single type of cancer, while others can be detected in several types of cancer. As with other cancer markers, Bcl-2 can be used for a variety of purposes, such as: screening a healthy population or a high risk population for the presence of cancer; making a diagnosis of cancer or of a specific type of cancer, such as ovarian cancer; determining the prognosis of a subject; and monitoring the course in a subject in remission or while receiving surgery, radiation, chemotherapy, or other cancer treatment.

Figure 3A:
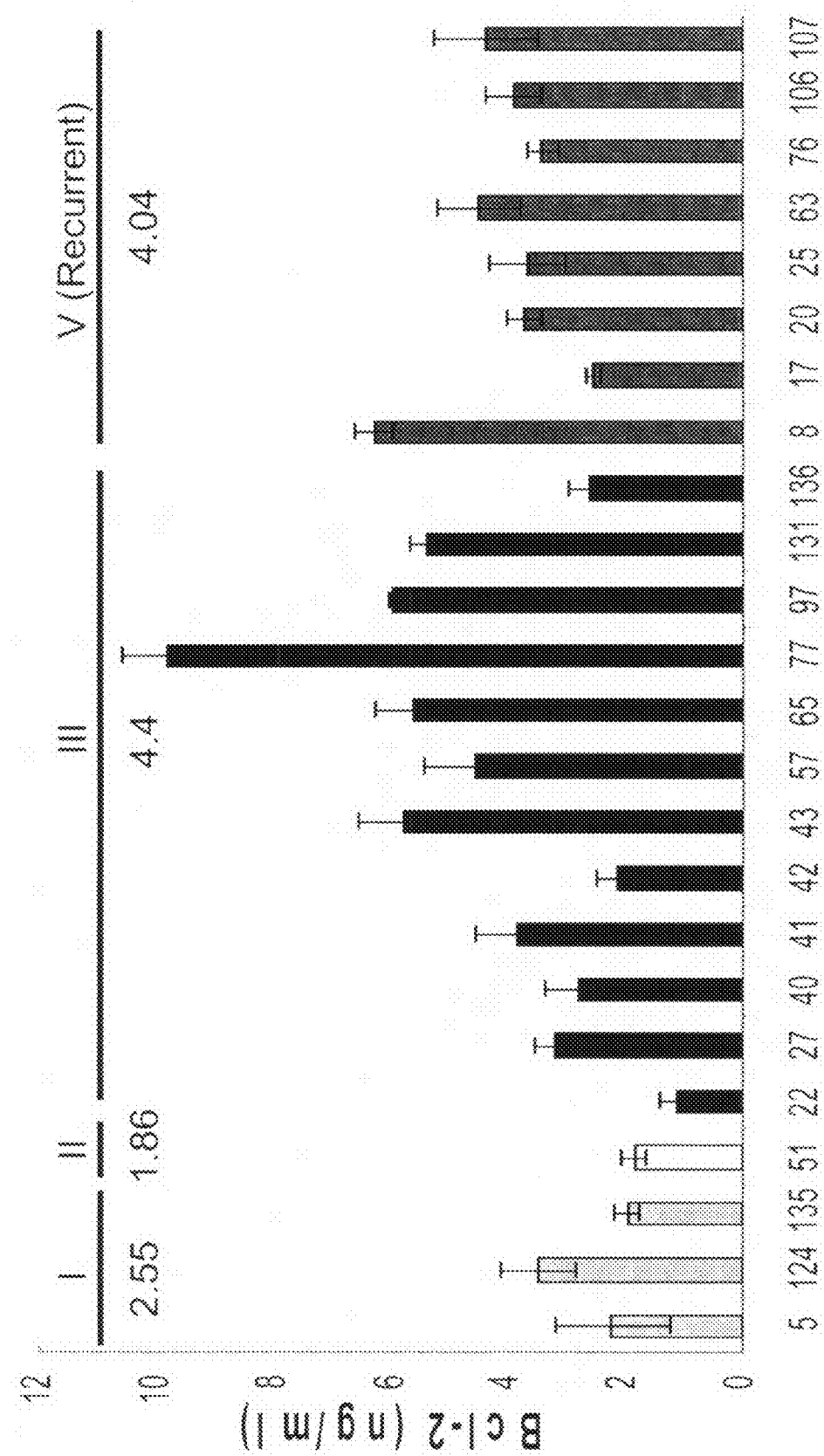
FIGS. 3A and 3B are histograms demonstrating that urinary Bcl-2 is related to tumor stage and grade, respectively. Levels of urinary Bcl-2 were plotted against tumor stage from all available histological ovarian cancer subtypes (serous, endometriod, mucinous). Stages I, II, III and V are represented by Roman numerals with groupings underneath. Though still considerably higher than normal controls, FIG.
Figure 3B:
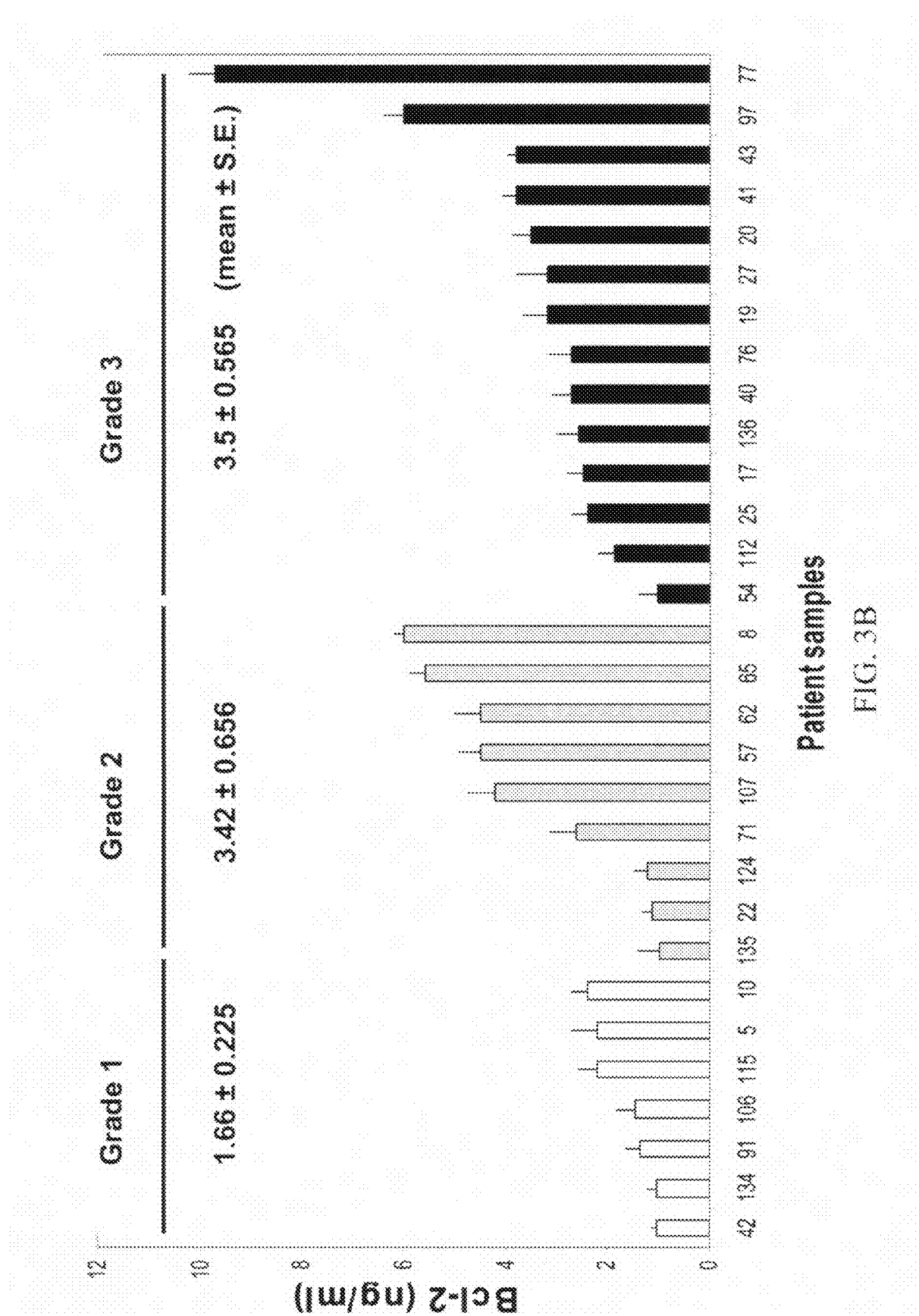

To assess whether urinary levels of Bcl-2 could be used to detect ovarian cancer, urine was collected from normal healthy volunteers (N=21) and from patients with ovarian (N=34) and primary peritoneal (N=2) cancer and measured in triplicate for Bcl-2 using commercially available ELISA kits (BenderMedSystems, catalog #BMS244/3) according to the manufacturer's instructions. The results were expressed as the average ng/ml Bcl-2±S.E. The average amount of Bcl-2 in the urine of healthy volunteers was 0.204 ng/ml while that from pre-surgical patients with cancer averaged 3.12 ng/ml, generally at least 10× greater than that found in normal controls. Student t-test analysis revealed a statistical difference between normal and cancer specimens at $p<0.00001$. Comparison of clinical parameters indicated that urinary levels of Bcl-2 correlated well with tumor stage and grade (FIGS. 3A and 3B).

Plasma samples from some of these same individuals above were examined in triplicate for CA125 levels by a commercially available ELISA (Bio-Quant, catalog #BQ1013T) according to the manufacturer's instructions. The sensitivity and specificity for elevated urinary Bcl-2 associated with ovarian cancer detection was almost 100% while blood levels of CA125>35 U/ml, the current standard for ovarian cancer detection, only correctly identified 68% of ovarian cancer patients.

To further test the accuracy for levels of urinary Bcl-2 to detect ovarian cancer, levels of urinary Bcl-2 were compared in those available ovarian cancer patients immediately prior to and within 2 weeks following initial debulking surgery (removal of all visible tumor). For those 7 patients where urine samples were collected before and after initial surgery, Bcl-2 levels decreased up to 100% following surgical removal of tumor. These data, then, suggest that the tumor is the source of Bcl-2 found elevated in the urine of patients with ovarian cancer. In addition, urine samples were collected from 5 of these 7 patients on subsequent follow up clinical visits ranging from 7 to 11 months following initial surgery and measured for Bcl-2. Urinary Bcl-2 levels remained low in 3 follow-up patients (#41, 43, 54) and became elevated in 2 patients (#5, 27). Preliminary chart review indicated that patients #41, 43, and 54 were undergoing chemotherapy at the time of follow-up visits and that their ovarian cancer disease was under control. In contrast, chart review suggests that patients #5, 27 had recurrent disease and that patient #27 underwent additional tumor debulking surgery. In agreement with the clinical information, urinary Bcl-2 levels remained reduced in patients undergoing chemotherapy and who had no apparent or minimal residual disease (#41,43,54). Likewise, elevated urinary Bcl-2 levels correlated with the presence of recurrent disease (#5, 27) and decreased with subsequent disease debulking (#27c).

Taken together, these data indicate that quantification of urinary Bcl-2 by ELISA-based assays appears to provide a novel, safe, sensitive, specific and economical method for the detection of ovarian cancer. Further, urinary levels of Bcl-2 can be used to monitor the presence of ovarian cancer throughout the course of disease and may predict therapeutic and prognostic outcome.

In one aspect, the invention includes a method for detecting cancer in a subject, comprising detecting the presence of Bcl-2 in a biological sample from the subject, such as urine, blood, peritoneal fluid, or ascites fluid, and wherein a level of Bcl-2 above a pre-determined threshold is indicative of cancer in the subject. Preferably, the detecting is not carried out by a qualitative slot-blot assay (such as that commercially available from BioRad).

The cancer detecting and/or monitoring using the methods, devices, and kits of the invention include, but are not limited to, breast cancer (e.g., infiltrating (invasive), pre-invasive, inflammatory, Paget's Disease, metastatic, or recurrent); gastrointestinal/digestive cancer (e.g., appendix, bile duct, colon, esophageal, gallbladder, gastric, intestinal, liver, pancreatic, rectal, and stomach); genitourinary/urinal cancer (e.g., adrenal, bladder, kidney, penile, prostate, testicular, and urinary); gynecological cancer (e.g., cervical, endometrial, fallopian tube, ovarian, uterine, vaginal, and vulvar); head and neck cancer (e.g., eye, head and neck, jaw, laryngeal, nasal cavity, oral cancer, pharyngeal, salivary gland, sinus, throat, thyroid, tongue, and tonsil); hematological/blood cancer (e.g., Hodgkin's disease, leukemia (acute lymphocytic leukemia, acute granulocytic leukemia, acute myelogenous leukemia, chronic lymphocytic leukemia, chronic myelogenous leukemia), multiple myeloma, lymphoma, and lymph node); musculoskeletal/soft tissue cancer (e.g., bone, osteosarcoma, melanoma, skin (basal cell, squamous cell), sarcoma (Ewing's sarcoma, Kaposis sarcoma)); neurological cancer (e.g., brain (astrocytoma, glioblastoma, glioma), pituitary gland, spinal cord)); and respiratory/lung cancer (e.g., lung, (adenocarcinoma, oat cell, non-small cell, small cell, squamous cell) and mesothelioma). In one embodiment, the cancer is ovarian cancer. In another embodiment, the cancer is a type selected from the group consisting of breast cancer, endometrial cancer, cervical cancer, lung cancer, colon cancer, prostate cancer, melanoma, glioblastoma, sarcoma, bladder cancer, and head and neck cancer.

In one embodiment of the method of the invention, the detecting comprises: (a) contacting the biological sample with a binding agent that binds Bcl-2 protein to form a complex; and (b) detecting the complex; and correlating the detected complex to the amount of Bcl-2 protein in the sample, wherein the presence of elevated Bcl-2 protein is indicative of cancer. In a specific embodiment, the detecting of (b) further comprises linking or incorporating a label onto the agent, or using ELISA-based immunoenzymatic detection.

Optionally, the methods of the invention further comprise detecting a biomarker of cancer in the same biological sample or a different biological sample obtained from the subject, before, during, or after said detecting of Bcl-2. In one embodiment, the biomarker of cancer is a biomarker of reproductive cancer, such as gynecological cancer. In another embodiment, the biomarker is CA125 or OVXI. The subject may have elevated CA125 level in the blood at the time the detecting of Bcl-2 is carried out, or the subject may not have an elevated CA125 level in the blood at the time the detecting of Bcl-2 is carried out.

In some embodiments, the subject is suffering from cancer, such as ovarian cancer, and the detecting is performed at several time points at intervals, as part of a monitoring of the subject before, during, or after the treatment of the cancer.

Optionally, the methods of the invention further comprise comparing the level of Bcl-2 in the biological sample with the level of Bcl-2 present in a normal control sample, wherein a higher level of Bcl-2 in the biological sample as compared to the level in the normal control sample is indicative of cancer such as ovarian cancer.

In some embodiments, the subject exhibits no symptoms of cancer at the time the detecting of Bcl-2 is carried out. In other embodiments, the subject exhibits one or more symptoms of cancer at the time the detecting of Bcl-2 is carried out. For example, with respect to gynecological cancer (e.g., ovarian cancer), the one or more symptoms of gynecological cancer include those selected from the group consisting of pelvic pain, abnormal vaginal bleeding, abdominal swelling or bloating, persistent back pain, persistent stomach upset, change in bowel or bladder pattern (such as constipation, diarrhea, blood in the stools, gas, thinner stools, frequency or urgency of urination, constipation), pain during intercourse, unintentional weight loss of ten or more pounds, vulva or vaginal abnormality (such as blister, change in skin color, or discharge), change in the breast (such as a lump, soreness, nipple discharge, dimpling, redness, or swelling), and fatigue.

In another embodiment, the invention includes a method for prognostic evaluation of a subject having, or suspected of having, cancer, comprising: a) determining the level of Bcl-2 in a biological sample obtained from the subject, such as urine, blood, or ascites fluid; b) comparing the level determined in step (a) to a range of Bcl-2 known to be present in a biological sample obtained from a normal subject that does not have cancer; and c) determining the prognosis of the subject based on the comparison of step (b), wherein a high level of Bcl-2 in step (a) indicates an aggressive form of cancer and, therefore, a poor prognosis.

The terms "detecting" or "detect" include assaying or otherwise establishing the presence or absence of the target Bcl-2 (Bcl-2 encoding nucleic acid sequence or Bcl-2 gene product (polypeptide)), subunits thereof, or combinations of agent bound targets, and the like, or assaying for, interrogating, ascertaining, establishing, or otherwise determining one or more factual characteristics of gynecological cancer, metastasis, stage, or similar conditions. The term encompasses diagnostic, prognostic, and monitoring applications for Bcl-2 and other cancer biomarkers. The term encompasses quantitative, semi-quantitative, and qualitative detection methodologies. In embodiments of the invention involving detection of Bcl-2 protein (as opposed to nucleic acid molecules encoding Bcl-2 protein), the detection method is preferably an ELISA-based method. Preferably, in the various embodiments of the invention, the detection method provides an output (i.e., readout or signal) with information concerning the presence, absence, or amount of Bcl-2 in a sample from a subject. For example, the output may be qualitative (e.g., "positive" or "negative"), or quantitative (e.g., a concentration such as nanograms per milliliter).

In an embodiment, the invention relates to a method for detecting cancer in a subject by quantitating Bcl-2 protein or encoding nucleic acids (DNA or RNA) in a biological sample such as urine from the subject, comprising (a) contacting (reacting) the biological sample with an antibody specific for Bcl-2 which is directly or indirectly labeled with a detectable substance; and (b) detecting the detectable substance.

In an embodiment, the invention relates to a method for diagnosing and/or monitoring cancer in a subject by quantitating Bcl-2 in a biological sample, such as urine or blood, from the subject, comprising (a) reacting the biological sample with an antibody specific for Bcl-2 which is directly or indirectly labeled with a delectable substance; and (b) detecting the detectable substance.

Embodiments of the methods of the invention involve (a) contacting a biological sample from a subject with an antibody specific for Bcl-2 which is directly or indirectly labeled with an enzyme; (b) adding a substrate for the enzyme wherein the substrate is selected so that the substrate, or a reaction product of the enzyme and substrate, forms fluorescent complexes; (c) quantitating Bcl-2 in the sample by measuring fluorescence of the fluorescent complexes; and (d) comparing the quantitated levels to that of a standard.

A preferred embodiment of the invention comprises the following steps:

(a) incubating a biological sample with a first antibody specific for Bcl-2 which is directly or indirectly labeled with a detectable substance, and a second antibody specific for Bcl-2 which is immobilized;

(b) separating the first antibody from the second antibody to provide a first antibody phase and a second antibody phase;

(c) detecting the detectable substance in the first or second antibody phase thereby quantitating Bcl-2 in the biological sample; and (d) comparing the quantitated Bcl-2 with a standard.

A standard used in a method of the invention may correspond to Bcl-2 levels obtained for samples from healthy control subjects, from subjects with benign disease (e.g., benign gynecological disease), subjects with early stage gynecological cancer, or from other samples of the subject. Increased levels of Bcl-2 as compared to the standard may be indicative of cancer, such as early or late stage ovarian cancer.

The invention also contemplates using the methods, devices, and kits described herein in conjunction with one or more additional markers ("biomarkers") for cancer. Therefore, the invention contemplates a method for analyzing a biological sample for the presence of Bcl-2 and analyzing the same sample, or another biological sample from the same subject, for other markers that are specific indicators of a cancer. The one or more additional markers may be detected before, during, and/or after detection of Bcl-2 is carried out. Examples of markers include CA125, LPA, and OVXI. In a preferred embodiment, the markers are Bcl-2 and CA125. The methods, devices, and kits described herein may be modified by including agents to detect the additional markers, or nucleic acids encoding the markers.

Cancer markers that may be used in conjunction with the invention include, but are not limited to: alpha fetoprotein (AFP), e.g., for pancreatic, kidney, ovarian, cervical, and testicular cancers; carcinogenic embryonic antigen (CEA), e.g., for lung, pancreatic, kidney, breast, uterine, liver, gastric, and colorectal cancers; carbohydrate antigen 15-3 (CA15-3), e.g., for lung, pancreatic, breast, ovarian, and liver cancers; carbohydrate antigen 19-9 (CA19-9), e.g., for lung, ovarian, uterine, liver, gastric, colorectal, and bile duct cancers; cancer antigen 125 (CA125), e.g., for lung, pancreas, breast, ovarian, cervical, uterine, liver, gastric, and colorectal cancers; free prostate specific antigen and prostate specific antigen-alpha (1) (PSA), for prostate cancer; free prostate specific antigen (PSAF), for prostate and colorectal cancers; prostate specific antigen-alpha(1)antichymotrypsin complex (PSAC), for prostate cancer; prostatic acid phosphatase (PAP), for prostate cancer; human thyroglobulin (hTG), for thyroid cancer or Wilm's tumor; human chorionic gonadaotropin beta (hCGb), e.g., for lung, pancreatic, kidney, ovarian, uterine, testicular, liver, colorectal, bladder, and brain cancers; ferritin (Ferr), e.g., for lung cancer, testicular cancer, cancer of the larynx, Burkitt's lymphoma, neuroblastoma, and leukemia; neuron specific enolase (NSE), for lung cancer, thyroid cancer, Wilm's tumor, and neuroblastoma; interleukin 2 (IL-2), for kidney cancer and multiple myeloma; interleukin 6 (IL-6), for kidney cancer, breast cancer, ovarian cancer, and multiple myeloma; beta 2 microglobulin (B2M), for kidney cancer, ovarian cancer, prostate cancer, leukemia, multiple myeloma, and lymphoma; and alpha 2 microglobulin (A2M), for prostate cancer. The selection of biological sample (such as blood or urine) in which the aforementioned cancer markers are diagnostic and/or prognostic can be readily determined by those skilled in the art.

As indicated above, the present invention provides a method for monitoring, diagnosing, or for the prognosis of cancer, such as ovarian cancer, in a subject by detecting Bcl-2 in a biological sample from the subject. In an embodiment, the method comprises contacting the sample with an antibody specific for Bcl-2 which is directly or indirectly labeled with a detectable substance, and detecting the detectable substance.

The methods of the invention may be used for the detection of either an over- or an under-abundance of Bcl-2 relative to a non-disorder state or the presence of a modified (e.g., less than full length) Bcl-2 which correlates with a disorder state (e.g., ovarian cancer), or a progression toward a disorder state. The methods described herein may be used to evaluate the probability of the presence of malignant or pre-malignant cells. Such methods can be used to detect tumors, quantitate their growth, and assistg in the diagnosis and prognosis of gynecological cancer. The methods can be used to detect the presence of cancer metastasis, as well as confirm the absence or removal of all tumor tissue following surgery, cancer chemotherapy, and/or radiation therapy. They can further be used to monitor cancer chemotherapy and tumor reappearance.

The methods of the invention are particularly useful in the diagnosis of early stage ovarian cancer (e.g., when the subject is asymptomatic) and for the prognosis of ovarian cancer disease progression and mortality. As illustrated herein, increased levels of Bcl-2 detected in a sample (e.g., urine, serum, plasma, whole blood, ascites) compared to a standard (e.g., levels for normal or benign disorders) are indicative of advanced disease stage, serous histological type, suboptimal debulking, large residual tumor, and/or increased risk of disease progression and mortality.

The terms "sample", "biological sample", and the like refer to a type of material known to or suspected of expressing or containing Bcl-2, such as urine. The test sample can be used directly as obtained from the source or following a pretreatment to modify the character of the sample. The sample can be derived from any biological source, such as tissues or extracts, including cells (e.g., tumor cells) and physiological fluids, such as, for example, whole blood, plasma, serum, peritoneal fluid, ascites, and the like. The sample can be obtained from animals, preferably mammals, most preferably humans. The sample can be pretreated by any method and/or can be prepared in any convenient medium that does not interfere with the assay. The sample can be treated prior to use, such as preparing plasma from blood, diluting viscous fluids, applying one or more protease inhibitors to samples such as urine (e.g., 4-(2 aminoethyl)-benzene sulfonyl fluoride, EDTA, leupeptin, and/or pepstatin), and the like. Sample treatment can involve filtration, distillation, extraction, concentration, inactivation of interfering components, the addition of reagents, and the like.

The presence of bcl-2 may be detected in a variety of biological samples, including tissues or extracts thereof. Preferably, Bcl-2 is detected in human urine.

In embodiments of the invention, the method described herein is adapted for diagnosing and monitoring gynecological cancer by quantitating Bcl-2 in biological samples from a subject. Preferably, the amount of Bcl-2 quantitated in a sample from a subject being tested is compared to levels quantitated for another sample or an earlier sample from the subject, or levels quantitated for a control sample. Levels for control samples from healthy subjects may be established by prospective and/or retrospective statistical studies. Healthy subjects who have no clinically evident disease or abnormalities may be selected for statistical studies. Diagnosis may be made by a finding of statistically different levels of Bcl-2 compared to a control sample or previous levels quantitated for the same subject.

The term "Bcl-2" refers to human B-cell lymphoma protein 2 (also known as B-cell CLL/lymphoma 2), an integral outer mitochondrial protein that blocks the apoptotic death of some cells such as lymphocytes (Cleary M. L. et al., *Cell*, 1986, 47(1):19-28; Tsujimoto Y. and Croce C. M., *Proc. Natl. Acad. Sci. USA*, 1986, 83:5214-5218, which are incorporated herein by reference in their entirety). The term "Bcl-2" includes nucleic acid sequences (e.g., GenBank Accession No. M14745; SEQ ID NO:1) encoding the Bcl-2 gene product (polypeptide), as well as the Bcl-2 polypeptide (e.g., GenBank Accession No. AAA35591; SEQ ID NO:2). The term includes all homologs, naturally occurring allelic variants, isoforms and precursors of human Bcl-2 of GenBank Accession Nos. M14745 and AAA35591. In general, naturally occurring allelic variants of human Bcl-2 will share significant sequence homology (70-90%) to the sequences shown in GenBank Accession Nos. M14745 and AAA35591. Allelic variants may contain conservative amino acid substitutions from the Bcl-2 sequence or will contain a substitution of an amino acid from a corresponding position in a Bcl-2 homologue. Two transcript variants, alpha and beta, produced by alternative splicing, differ in their C-terminal ends. The alpha variant (GenBank Accession No. NP_000624 (SEQ ID NO:4); and GenBank Accession No. NM_000633 (SEQ ID NO:3)) represents the longer transcript and encodes the longer isoform (alpha), and beta being the shorter (GenBank Accession No. NM_000648 (SEQ ID NO:6); GenBank Accession No. NP_000657 (SEQ ID NO:5). The beta variant differs in the 3' UTR and coding region compared to the alpha variant, as well as the C-terminal end. In a particular embodiment, the methods, devices, and kits of the invention are specific for Bcl-2 (e.g., SEQ ID NOs: 1, 2, 3, 4, 5, and/or 6), but not nucleic acid molecules or polypeptides known in the art as "Bcl-2-like" molecules (e.g., employing binding agents specific for (e.g., immunoreactive with) Bcl-2, but not reactive with Bcl-2 like molecules), such as those described in Ruben et al., U.S. Patent Application Publication 2002/0106731 A1, published Aug. 8, 2002, which is incorporated herein by reference in its entirety.

The terms "subject" and "patient" are used interchangeably herein to refer to a warm-blooded animal, such as a mammal, which may be afflicted with cancer. In some cancers, the subject is human or non-human mammalian female. In other cancers, the subject is a human or non-human mammalian male.

Agents that are capable of detecting Bcl-2 in the biological samples of subjects are those that interact or bind with the Bcl-2 polypeptide or the nucleic acid molecule encoding Bcl-2. Examples of such agents (also referred to herein as binding agents) include, but are not limited to, Bcl-2 antibodies or fragments thereof that bind Bcl-2, Bcl-2 binding partners, and nucleic acid molecules that hybridize to the nucleic acid molecules encoding Bcl-2 polypeptides. Preferably, the binding agent is labeled with a detectable substance (e.g., a detectable moiety). The binding agent may itself function as a label.

Bcl-2 Antibodies

Antibodies specific for Bcl-2 that are used in the methods of the invention may be obtained from scientific or commercial sources. Alternatively, isolated native Bcl-2 or recombinant Bcl-2 may be utilized to prepare antibodies, monoclonal or polyclonal antibodies, and immunologically active fragments (e.g., a Fab or $(Fab)_2$ fragment), an antibody heavy chain, an antibody light chain, humanized antibodies, a genetically engineered single chain F, molecule (Ladne et al., U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. Preferably, antibodies used in the methods of the invention are reactive against Bcl-2 if they bind with a $K_a$ of greater than or equal to $10^7$ M. In a sandwich immunoassay of the invention, mouse polyclonal antibodies and rabbit polyclonal antibodies are utilized.

In order to produce monoclonal antibodies, a host mammal is inoculated with a Bcl-2 protein or peptide and then boosted. Spleens are collected from inoculated mammals a few days after the final boost. Cell suspensions from the spleens are fused with a tumor cell in accordance with the general method described by Kohler and Milstein (*Nature*, 1975, 256:495-497). In order to be useful, a peptide fragment must contain sufficient amino acid residues to define the epitope of the Bcl-2 molecule being detected.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule. The peptide fragments may be synthesized by methods known in the art. Some suitable methods are described by Stuart and Young in "Solid Phase Peptide Synthesis," Second Edition, Pierce Chemical Company (1984).

Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (Goding in, Monoclonal Antibodies: Principles and Practice, 2d ed., pp. 104-126, Orlando, Fla., Academic Press). It is preferable to use purified antibodies or purified fragments of the antibodies having at least a portion of a Bcl-2 binding region, including such as Fv, $F(ab')_2$, Fab fragments (Harlow and Lane, 1988, Antibody Cold Spring Harbor) for the detection of Bcl-2 in the fluids of gynecological cancer patients or those at risk, preferably in the urine or blood of ovarian cancer patients.

For use in detection and/or monitoring of cancer, the purified antibodies can be covalently attached, either directly or via linker, to a compound which serves as a reporter group to permit detection of the presence of Bcl-2. A variety of different types of substances can serve as the reporter group, including but not limited to enzymes, dyes, radioactive metal and non-metal isotopes, fluorogenic compounds, fluorescent compounds, etc. Methods for preparation of antibody conjugates of the antibodies (or fragments thereof) of the invention useful for detection, monitoring are described in U.S. Pat. Nos. 4,671,958; 4,741,900 and 4,867,973.

In one aspect of the invention, preferred binding epitopes may be identified from a known Bcl-2 gene sequence and its encoded amino acid sequence and used to generate Bcl-2 antibodies with high binding affinity. Also, identification of binding epitopes on Bcl-2 can be used in the design and construction of preferred antibodies. For example, a DNA encoding a preferred epitope on Bcl-2 may be recombinantly expressed and used to select an antibody which binds selectively to that epitope. The selected antibodies then are exposed to the sample under conditions sufficient to allow specific binding of the antibody to the specific binding epitope on Bcl-2 and the amount of complex formed then detected. Specific antibody methodologies are well understood and described in the literature. A more detailed description of their preparation can be found, for example, in Practical Immunology, Butt, W. R., ed., Marcel Dekker, New York, 1984.

The present invention also contemplates the detection of Bcl-2 antibodies. Bcl-2 is a gynecological cancer-specific marker. Thus, detection of Bcl-2 antibodies in biological fluids of a subject may enable the diagnosis of gynecological cancer.

Protein Binding Assays

Antibodies specifically reactive with Bcl-2, or derivatives, such as enzyme conjugates or labeled derivatives, may be used to detect Bcl-2 in various biological samples, for example they may be used in any known immunoassays which rely on the binding interaction between an antigenic determinant of a protein and the antibodies. Examples of such assays are radioimmunoassays, enzyme immunoassay (e.g., ELISA), immunofluorescence, immnunoprecipitation, latex agglutination, hemagglutination, and histochemical tests.

An antibody specific for Bcl-2 can be labeled with a detectable substance and localized in biological samples based upon the presence of the detectable substance. Examples of detectable substances include, but are not limited to, the following radioisotopes (e.g., $^3H$, $^{14}C$, $^{35}S$, $^{125}I$, $^{131}I$), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinestease), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Indirect methods may also be employed in which the primary antigen-antibody reaction is amplified by the introduction of a second antibody, having specificity for the antibody reactive against Bcl-2. By way of example, if the antibody having specificity against Bcl-2 is a rabbit IgG antibody, the second antibody may be goat anti-rabbit gamma-globulin labeled with a detectable substance as described herein.

Methods for conjugating or labeling the antibodies discussed above may be readily accomplished by one of ordinary skill in the art. (See, for example, Imman, Methods In Enzymology, Vol. 34, Affinity Techniques, Enzyme Purification: Part B, Jakoby and Wichek (eds.), Academic Press, New York, p. 30, 1974; and Wilchek and Bayer, "The Avidin-Biotin Complex in Bioanalytical Applications," Anal. Biochem. 171:1-32, 1988, regarding methods for conjugating or labeling the antibodies with an enzyme or ligand binding partner).

Time-resolved fluorometry may be used to detect a signal. For example, the method described in Christopoulos T. K. and Diamandis E. P., *Anal. Chem.,* 1992:64:342-346 may be used with a conventional time-resolved fluorometer.

Therefore, in accordance with an embodiment of the invention, a method is provided wherein a Bcl-2 antibody is labeled with an enzyme, a substrate for the enzyme is added wherein the substrate is selected so that the substrate, or a reaction product of the enzyme and substrate, forms fluorescent complexes with a lanthanide metal. A lanthanide metal is added and Bcl-2 is quantitated in the sample by measuring fluorescence of the fluorescent complexes. The antibodies specific for Bcl-2 may be directly or indirectly labeled with an enzyme. Enzymes are selected based on the ability of a substrate of the enzyme, or a reaction product of the enzyme and substrate, to complex with lanthanide metals such as europium and terbium. Examples of suitable enzymes include alkalline phosphatase and beta-galactosidase. Preferably, the enzyme is akline phosphatase. The Bcl-2 antibodies may also be indirectly labeled with an enzyme. For example, the antibodies may be conjugated to one partner of a ligand binding pair, and the enzyme may be coupled to the other partner of the ligand binding pair. Representative examples include avidin-biotin, and riboflavin-riboflavin binding protein. Preferably the antibodies are biotinylated, and the enzyme is coupled to streptavidin.

In an embodiment of the method, antibody bound to Bcl-2 in a sample is detected by adding a substrate for the enzyme. The substrate is selected so that in the presence of a lanthanide metal (e.g., europium, terbium, samarium, and dysprosium, preferably europium and terbium), the substrate or a reaction product of the enzyme and substrate, forms a fluorescent complex with the lanthanide metal. Examples of enzymes and substrates for enzymes that provide such fluorescent complexes are described in U.S. Pat. No. 5,3112,922 to Diamandis. By way of example, when the antibody is directly or indirectly labeled with alkalline phosphatase, the substrate employed in the method may be 4-methylumbeliferyl phosphate, or 5-fluorpsalicyl phosphate. The fluorescence intensity of the complexes is typically measured using a time-resolved fluorometer, e.g., a CyberFluor 615 Immoanalyzer (Nordion International, Kanata Ontario).

The sample, antibody specific for Bcl-2, or Bcl-2, may be immobilized on a carrier. Examples of suitable carriers are agarose, cellulose, dextran, Sephadex, Sepharose, liposomes, carboxymethyl cellulose polystyrene, filter paper, ion-exchange resin, plastic film, plastic tube, glass beads, polyamine-methyl vinyl ether-maleic acid copolymer, amino acid copolymer, ethylene-maleic acid copolymer, nylon, silk, etc. The carrier may be in the shape of, for example, a tube, test plate, well, beads, disc, sphere, etc. The immobilized antibody may be prepared by reacting the material with a suitable insoluble carrier using known chemical or physical methods, for example, cyanogen bromide coupling.

In accordance with an embodiment, the present invention provides a mode for determining Bcl-2 in an appropriate sample such as urine by measuring Bcl-2 by immunoassay. It will be evident to a skilled artisan that a variety of immunoassay methods can be used to measure Bcl-2. In general, a Bcl-2 immunoassay method may be competitive or rioncompetitive. Competitive methods typically employ an immobilized or immobilizable antibody to Bcl-2 (anti-Bcl-2) and a labeled form of Bcl-2. Sample Bcl-2 and labeled Bcl-2 compete for binding to anti-Bcl-2. After separation of the resulting labeled Bcl-2 that has become bound to anti-Bcl-2 (bound fraction) from that which has remained unbound (unbound fraction), the amount of the label in either bound or unbound fraction is measured and may be correlated with the amount of Bcl-2 in the biological sample in any conventional manner, e.g., by comparison to a standard curve.

Preferably, a noncompetitive method is used for the determination of Bcl-2, with the most common method being the "sandwich" method. In this assay, two anti-Bcl-2 antibodies are employed. One of the anti-Bcl-2 antibodies is directly or indirectly labeled (also referred to as the "detection antibody") and the other is immobilized or immobilizable (also referred to as the "capture antibody"). The capture and detection antibodies can be contacted simultaneously or sequentially with the biological sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the liquid test mixture, and the label is measured in at least a portion of the separated capture antibody phase or the remainder of the liquid test mixture. Generally, it is measured in the capture antibody phase since it comprises Bcl-2 bound by ("sandwiched" between) the capture and detection antibodies.

In a typical two-site immunometric assay for Bcl-2, one or both of the capture and detection antibodies are polyclonal antibodies. The label used in the detection antibody can be selected from any of those known conventionally in the art. As with other embodiments of the protein detection assay, the label can be an enzyme or a chemiluminescent moiety, for example, or a radioactive isotope, a fluorophore, a detectable ligand (e.g., detectable by a secondary binding by a labeled binding partner for the ligand), and the like. Preferably, the antibody is labeled with an enzyme that is detected by adding a substrate that is selected so that a reaction product of the enzyme and substrate forms fluorescent complexes. The capture antibody is selected so that it provides a mode for being separated from the remainder of the test mixture. Accordingly, the capture antibody can be introduced to the assay in an already immobilized or insoluble form, or can be in an immobilizable form, that is, a form which enables immobilization to be accomplished subsequent to introduction of the capture antibody to the assay. An immobilized capture antibody can comprise an antibody covalently or noncovalently attached to a solid phase such as a magnetic particle, a latex particle, a microtiter multi-well plate, a bead, a cuvette, or other reaction vessel. An example of an immobilizable capture antibody is an antibody that has been chemically modified with a ligand moiety, e.g., a hapten, biotin, or the like, and that can be subsequently immobilized by contact with an immobilized form of a binding partner for the ligand, e.g., an antibody, avidin, or the like. In an embodiment, the capture antibody can be immobilized using a species specific antibody for the capture antibody that is bound to the solid phase.

A particular sandwich immunoassay method of the invention employs two antibodies reactive against Bcl-2, a second antibody having specificity against an antibody reactive against Bcl-2 labeled with an enzymatic label, and a fluorogenic substrate for the enzyme. In an embodiment, the enzyme is alkalline phosphatase (ALP) and the substrate is 5-fluorosalicyl phosphate. ALP cleaves phosphate out of the fluorogenic substrate, 5-fluorosalicyl phosphate, to produce 5-fluorosalicylic acid (FSA). 5-Fluorosalicylic acid can then form a highly fluorescent ternary complex of the form FSA-Tb(3+)-EDTA, which can be quantified by measuring the $Tb^{3+}$ fluorescence in a time-resolved mode. Fluorescence intensity is typically measured using a time-resolved fluorometry as described herein.

The above-described immunoassay methods and formats are intended to be exemplary and are not limiting since, in general, it will be understood that any immunoassay method or format can be used in the present invention.

The protein detection methods, devices, and kits of the invention can utilize nanowire sensor technology (Zhen et al., *Nature Biotechnology,* 2005, 23(10):1294-1301; Lieber et al., *Anal. Chem.,* 2006, 78(13):4260-4269, which are incorporated herein by reference) or microcantilever technology (Lee et al., *Biosens. Bioelectron,* 2005, 20(10):2157-2162; Wee et al., *Biosens. Bioelectron.,* 2005, 20(10):1932-1938; Campbell and Mutharasan, *Biosens. Bioelectron.,* 2005, 21(3):462-473; Campbell and Mutharasan, *Biosens. Bioelectron.,* 2005, 21(4):597-607; Hwang et al., *Lab Chip,* 2004, 4(6):547-552; Mukhopadhyay et al., *Nano. Lett.,* 2005, 5(12):2835-2388, which are incorporated herein by reference) for detection of Bcl-2 in samples. In addition, Huang et al. describe a prostate specific antigen immunoassay on a commercially available surface plasmon resonance biosensor (*Biosens. Bioelectron.,* 2005, 21(3):483-490, which is incorporated herein by reference) which may be adapted for detection of Bcl-2. High-sensitivity miniaturized immunoassays may also be utilized for detection of Bcl-2 (Cesaro-Tadic et al, *Lab Chip,* 2004, 4(6):563-569; Zimmerman et al., *Biomed. Microdevices,* 2005, 7(2):99-110, which are incorporated herein by reference).

Nucleic Acids

Nucleic acids including naturally occurring nucleic acids, oligonucleotides, antisense oligonucleotides, and synthetic oligonucleotides that hybridize to the nucleic acid encoding Bcl-2, are useful as agents to detect the presence of Bcl-2 in the biological samples of gynecological cancer patients or those at risk of gynecological cancer, preferably in the urine of ovarian cancer patients or those at risk of ovarian cancer. The present invention contemplates the use of nucleic acid sequences corresponding to the coding sequence of Bcl-2 and to the complementary sequence thereof, as well as sequences complementary to the Bcl-2 transcript sequences occurring further upstream or downstream from the coding sequence (e.g., sequences contained in, or extending into, the 5' and 3' untranslated regions) for use as agents for detecting the expression of Bcl-2 in biological samples of gynecological cancer patients, or those at risk of gynecological cancer, preferably in the urine of ovarian cancer patients or those at risk of ovarian cancer.

The preferred oligonucleotides for detecting the presence of Bcl-2 in biological samples are those that are complementary to at least part of the cDNA sequence encoding Bcl-2. These complementary sequences are also known in the art as "antisense" sequences. These oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine) and U (uracil), or modified oligonucleotide species, substituting, for example, a methyl group or a sulfur atom for a phosphate oxygen in the inter-nucleotide phosohodiester linkage. Additionally, these nucleotides themselves, and/or the ribose moieties may be modified.

The oligonucleotides may be synthesized chemically, using any of the known chemical oligonucleotide synthesis methods well described in the art. For example, the oligonucleotides can be prepared by using any of the commercially available, automated nucleic acid synthesizers. Alternatively, the oligonucleotides may be created by standard recombinant DNA techniques, for example, inducing transcription of the noncoding strand. The DNA sequence encoding Bcl-2 may be inverted in a recombinant DNA system, e.g., inserted in reverse orientation downstream of a suitable promoter, such that the noncoding strand now is transcribed.

Although any length oligonucleotide may be utilized to hybridize to a nucleic acid encoding Bcl-2, oligonucleotides typically within the range of 8-100 nucleotides are preferred. Most preferable oligonucleotides for use in detecting Bcl-2 in urine samples are those within the range of 15-50 nucleotides.

The oligonucleotide selected for hybridizing to the Bcl-2 nucleic acid molecule, whether synthesized chemically or by recombinant DNA technology, is then isolated and purified using standard techniques and then preferably labeled (e.g., with $^{35}S$ or $^{32}P$) using standard labeling protocols.

The present invention also contemplates the use of oligonucleotide pairs in polymerize chain reactions (PCR) to detect the expression of Bcl-2 in biological samples. The oligonucleotide pairs include a forward Bcl-2 primer and a reverse Bcl-2 primer.

The presence of Bcl-2 in a sample from a patient may be determined by nucleic acid hybridization, such as but not limited to Northern blot analysis, dot blotting, Southern blot analysis, fluorescence in situ hybridization (FISH), and PCR. Chromatography, preferably HPLC, and other known assays may also be used to determine messenger RNA levels of Bcl-2 in a sample.

The Bcl-2 encoding nucleic acid molecules conceivably may be found in the biological fluids inside a Bcl-positive cancer cell that is being shed or released in the fluid under investigation.

In one aspect, the present invention contemplates the use of nucleic acids as agents for detecting Bcl-2 in biological samples of patients, wherein the nucleic acids are labeled. The nucleic agents may be labeled with a radioactive label, a fluorescent label, an enzyme, a chemiluminescent tag, a calorimetric tag or other labels or tags that are discussed above or that are known in the art.

In another aspect, the present invention contemplates the use of Northern blot analysis to detect the presence of Bcl-2 mRNA in a sample of bodily fluid. The first step of the analysis involves separating a sample containing Bcl-2 nucleic acid by gel electrophoresis. The dispersed nucleic acids are then transferred to a nitrocellulose filter or another filter. Subsequently, the labeled oligonucleotide is exposed to the filter under suitable hybridizing conditions, e.g., 50% formamide, 5×SSPE, 2×Denhardt's solution, 0.1% SDS at 42° C., as described in Molecular Cloning: A Laboratory Manual, Maniatis et al. (1982, CSH Laboratory). Other useful procedures known in the art include solution hybridization, dot and slot RNA hybridization, and probe based microarrays. Measuring the radioactivity of hybridized fragments, using standard procedures known in the art quantitates the amount of Bcl-2 nucleic acid present in the biological fluid of a patient.

Dot blotting involves applying samples containing the nucleic acid of interest to a membrane. The nucleic acid can be denatured before or after application to the membrane. The membrane is incubated with a labeled probe. Dot blot procedures are well known to the skilled artisan and are described more fully in U.S. Pat. Nos. 4,582,789 and 4,617,261, the disclosures of which are incorporated herein by reference.

Polymerase chain reaction (PCR) is a process for amplifying one or more specific nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired-amount of the sequence. The skilled artisan to detect the presence of desired sequence (U.S. Pat. No. 4,683,195) routinely uses polymerase chain reaction.

A specific example of PCR that is routinely performed by the skilled artisan to detect desired sequences is reverse transcript PCR (RT-PCR; Saiki et al., *Science,* 1985, 230:1350; Scharf et al., *Science,* 1986, 233:1076). RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan.

In a preferred embodiment, the methods of detecting Bcl-2 nucleic acid in biological fluids of gynecological cancer patients or those at risk thereof, preferably urine of ovarian cancer patients or those at risk thereof, include Northern blot analysis, dot blotting, Southern blot analysis, FISH, and PCR.

Devices

The methods of the invention can be carried out on a solid support. The solid supports used may be those which are conventional for the purpose of assaying an analyte in a biological sample, and are typically constructed of materials such as cellulose, polysaccharide such as Sephadex, and the like, and may be partially surrounded by a housing for protection and/or handling of the solid support. The solid support can be rigid, semi-rigid, flexible, elastic (having shape-memory), etc., depending upon the desired application. Bcl-2 can be detected in a sample in vivo or in vitro (ex vivo). When, according to an embodiment of the invention, the amount of Bcl-2 in a sample is to be determined without removing the sample from the body (i.e., in vivo), the support should be one which is harmless to the subject and may be in any form convenient for insertion into an appropriate part of the body. For example, the support may be a probe made of polytetrafluoroethylene, polystyrene or other rigid non-harmful plastic material and having a size and shape to enable it to be introduced into a subject. The selection of an appropriate inert support is within the competence of those skilled in the art, as are its dimensions for the intended purpose.

A contacting step in the assay (method) of the invention can involve contacting, combining, or mixing the biological sample and the solid support, such as a reaction vessel, microvessel, tube, microtube, well, multi-well plate, or other solid support. In an embodiment of the invention, the solid support to be contacted with the biological sample (e.g., urine) has an absorbent pad or membrane for lateral flow of the liquid medium to be assayed, such as those available from Millipore Corp. (Bedford, Mass.), including but not limited to Hi-Flow Plus™ membranes and membrane cards, and SureWick™ pad materials.

The diagnostic device useful in carrying out the methods of the invention can be constructed in any form adapted for the intended use. Thus, in one embodiment, the device of the invention can be constructed as a disposable or reusable test strip or stick to be contacted with a biological sample such as urine or blood for which Bcl-2 level is to be determined. In another embodiment, the device can be constructed using art recognized micro-scale manufacturing techniques to produce needle-like embodiments capable of being implanted or injected into an anatomical site, such as the peritoneal cavity, for indwelling diagnostic applications. In other embodiments, devices intended for repeated laboratory use can be constructed in the form of an elongated probe.

In preferred embodiments, the devices of the invention comprise a solid support (such as a strip or dipstick), with a surface that functions as a lateral flow matrix defining a flow path for a biological sample such as urine, whole blood, serum, plasma, peritoneal fluid, or ascites.

Immunochromatographic assays, also known as lateral flow test strips or simply strip tests, for detecting various analytes of interest, have been known for some time, and may be used for detection of Bcl-2. The benefits of lateral flow tests include a user-friendly format, rapid results, long-term stability over a wide range of climates, and relatively low cost to manufacture. These features make lateral flow tests ideal for applications involving home testing, rapid point of care testing, and testing in the field for various analytes. The principle behind the test is straightforward. Essentially, any ligand that can be bound to a visually detectable solid support, such as dyed microspheres, can be tested for, qualitatively, and in many cases even semi-quantitatively. For example, a one-step lateral flow immunostrip for the detection of free and total prostate specific antigen in serum is described in Fernandez-Sanchez et al. (J. *Immuno. Methods,* 2005, 307(1-2):1-12, which is incorporated herein by reference) and may be adapted for detection of Bcl-2 in a biological sample such as blood or urine.

Some of the more common immunochromatographic assays currently on the market are tests for pregnancy (as an over-the-counter (OTC) test kit), Strep throat, and Chlamydia. Many new tests for well-known antigens have been recently developed using the immunochromatographic assay method. For instance, the antigen for the most common cause of community acquired pneumonia has been known since 1917, but a simple assay was developed only recently, and this was done using this simple test strip method (Murdoch, D. R. et al. *J Clin Microbiol,* 2001, 39:3495-3498). Human immunodeficiency virus (HIV) has been detected rapidly in pooled blood using a similar assay (Soroka, S. D. et al. *J Clin Virol,* 2003, 27:90-96). A nitrocellulose membrane card has also been used to diagnose schistosomiasis by detecting the movement and binding of nanoparticles of carbon (van Dam, G. J. et al. *J Clin Microbiol,* 2004, 42:5458-5461).

The two common approaches to the immunochromatographic assay are the non-competitive (or direct) and competitive (or competitive inhibition) reaction schemes (TechNote #303, Rev. #001, 1999, Bangs Laboratories, Inc., Fishers, Ind.). The direct (double antibody sandwich) format is typically used when testing for larger analytes with multiple antigenic sites such as luteinizing hormone (LH), human chorionic gonadotropin (hCG), and HIV. In this instance, less than an excess of sample analyte is desired, so that some of the microspheres will not be captured at the capture line, and will continue to flow toward the second line of immobilized antibodies, the control zone. This control line uses species-specific anti-immunoglobulin antibodies, specific for the conjugate antibodies on the microspheres. Free antigen, if present, is introduced onto the device by adding sample (urine, serum, etc.) onto a sample addition pad. Free antigen then binds to antibody-microsphere complexes. Antibody 1, specific for epitope 1 of sample antigen, is coupled to dye microspheres and dried onto the device. When sample is added, microsphere-antibody complex is rehydrated and carried to a capture zone and control lines by liquid. Antibody 2, specific for a second antigenic site (epitope 2) of sample antigen, is dried onto a membrane at the capture line. Antibody 3, a species-specific, anti-immunoglobulin antibody that will react with antibody 1, is dried onto the membrane at the control line. If antigen is present in the sample (i.e., a positive test), it will bind by its two antigenic sites, to both antibody 1 (conjugated to microspheres) and antibody 2 (dried onto membrane at the capture line). Antibody 1-coated microspheres are bound by antibody 3 at the control line, whether antigen is present or not. If antigen is not present in the sample (a negative test), microspheres pass the capture line without being trapped, but are caught by the control line.

The competitive reaction scheme is typically used when testing for small molecules with single antigenic determinants, which cannot bond to two antibodies simultaneously. As with double antibody sandwich assay, free antigen, if present is introduced onto the device by adding sample onto a sample pad. Free antigen present in the sample binds to an antibody-microsphere complex. Antibody 1 is specific for sample antigen and couple to dyed microspheres. An antigen-carrier molecule (typically BSA) conjugate is dried onto a membrane at the capture line. Antibody 2 (Ab2) is dried onto the membrane at the control line, and is a species-specific anti-immunoglobulin that will capture the reagent particles and confirm that the test is complete. If antigen is present in the sample (a positive test), antibody on microspheres (Ab1) is already saturated with antigen from sample and, therefore, antigen conjugate bound at the capture line does not bind to it. Any microspheres not caught by the antigen carrier molecule can be caught by Ab2 on the control line. If antigen is not present in the sample (a negative test), antibody-coated dyed microspheres are allowed to be captured by antigen conjugate bound at the capture line.

Normally, the membranes used to hold the antibodies in place on these devices are made of primary hydrophobic materials, such as nitrocellulose. Both the microspheres used as the solid phase supports and the conjugate antibodies are hydrophobic, and their interaction with the membrane allows them to be effectively dried onto the membrane.

Samples and/or Bcl-2-specific binding agents may be arrayed on the solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or -1536 well, plates (or trays). Optionally, Bcl-2-specific binding agents may be immobilized on the solid support.

Detection of Bcl-2 and cancer biomarkers, and other assays that are to be carried out on samples, can be carried out simultaneously or sequentially with the detection of other target molecules, and may be carried out in an automated fashion, in a high-throughput format.

The Bcl-2-specific binding agents can be deposited but "free" (non-immobilized) in the conjugate zone, and be immobilized in the capture zone of a solid support. The Bcl-2-specific binding agents may be immobilized by non-specific adsorption onto the support or by covalent bonding to the support, for example. Techniques for immobilizing binding agents on supports are known in the art and are described for example in U.S. Pat. Nos. 4,399,217, 4,381,291, 4,357,311, 4,343,312 and 4,260,678, which are incorporated herein by reference. Such techniques can be used to immobilize the binding agents in the invention. When the solid support is polytetrafluoroethylene, it is possible to couple hormone antibodies onto the support by activating the support using sodium and ammonia to aminate it and covalently bonding the antibody to the activated support by means of a carbodiimide reaction (yon Klitzing, Schultek, Strasburger, Fricke and Wood in "Radioimmunoassay and Related Procedures in Medicine 1982", International Atomic Energy Agency, Vienna (1982), pages 57-62.).

The diagnostic device of the invention can utilize lateral flow strip (LFS) technology, which has been applied to a number of other rapid strip assay systems, such as over-the-counter early pregnancy test strips based on antibodies to human chorionic gonadotropin (hCG). As with many other diagnostic devices, the device utilizes a binding agent to bind the target molecule (Bcl-2). The device has an application zone for receiving a biological sample such as blood or urine, a labeling zone containing label which binds to Bcl-2 in the sample, and a detection zone where Bcl-2 label is retained.

Binding agent retained in the detection zone gives a signal, and the signal differs depending on whether Bcl-2 levels in the biological sample are lower than, equal to, or greater than a given threshold concentration. For example, in the case of urinary Bcl-2 for the detection of ovarian cancer, the threshold concentration may be between 0 ng/ml and 2.0 ng/ml. In another embodiment, in the case of urinary Bcl-2 for the detection of ovarian cancer, the threshold concentration is 1.8 ng/ml. A sample from a subject having a Bcl-2 level equal to or greater than the given reference Bcl-2 concentration can be referred to as a "threshold level", "threshold amount", or "threshold sample". The application zone in the device is suitable for receiving the biological sample to be assayed. It is typically formed from absorbent material such as blotting paper. The labeling zone contains binding agent that binds to any Bcl-2 in the sample. In one embodiment, the binding agent is an antibody (e.g., monoclonal antibody, polyclonal antibody, antibody fragment). For ease of detection, the binding agent is preferably in association with a label that provides a signal that is visible to the naked eye, e.g., it is tagged with a fluorescent tag or a colored tag such as conjugated colloidal gold, which is visible as a pink color.

The detection zone retains Bcl-2 to which the binding agent has bound. This will typically be achieved using an immobilized binding agent such as an immobilized antibody. Where the binding agent in the labeling zone and the detection zone are both antibodies, they will typically recognize different epitopes on the target molecule (Bcl-2 protein). This allows the formation of a "sandwich" comprising antibody-Bcl-2-antibody.

The detection zone is downstream of the application zone, with the labelling zone typically located between the two. A sample will thus migrate from the application zone into the labeling zone, where any in the sample binds to the label. Bcl-2-binding agent-complexes continue to migrate into the detection zone together with excess binding agent. When the Bcl-2-binding agent complex encounters the capture reagent, the complex is retained whilst the sample and excess binding agent continue to migrate. As Bcl-2 levels in the sample increase, the amount of binding agent (in the form of Bcl-2-binding agent complex) retained in the detection zone increases proportionally.

In preferred embodiments, the device of the invention has the ability to distinguish between samples according to the threshold concentration. This can be achieved in various ways.

One type of device includes a reference zone that includes a signal of fixed intensity against which the amount of binding agent retained in the detection zone can be compared—when the signal in the detection zone equals the signal in the reference zone, the sample is a threshold sample; when the signal in the detection zone is less intense than the reference zone, the sample contains less Bcl-2 than a threshold sample; when the signal in the detection zone is more intense than the reference zone, the sample contains more Bcl-2 than a threshold sample.

A suitable reference zone can be prepared and calibrated without difficulty. For this type of device, the binding agent will generally be present in excess to Bcl-2 in the sample, and the reference zone may be upstream or, preferably, downstream of the detection zone. The signal in the reference zone will be of the same type as the signal in the detection zone, i.e., they will typically both be visible to the naked eye, e.g., they will use the same tag. A preferred reference zone in a device of this type comprises immobilized protein (e.g., bovine serum albumin) which is tagged with colloidal gold.

In another device of the invention, the reference zone is downstream of the detection zone and includes a reagent which captures binding agent (e.g., an immobilised anti-binding agent antibody). Binding agent that flows through the device is not present in excess, but is at a concentration such that 50% of it is bound by a sample having Bcl-2 at the threshold concentration. In a threshold sample, therefore, 50% of the binding agent will be retained in the detection zone and 50% in the reference zone. If the Bcl-2 level in the sample is greater than in a threshold sample, less than 50% of the binding agent will reach the reference zone and the detection zone will give a more intense signal than the reference zone; conversely, if the Bcl-2 level in the sample is less than in a threshold sample, less than 50% of the binding agent will be retained in the detection zone and the reference zone will give a more intense signal than the detection zone.

In another device of the invention which operates according to similar principles, the reference zone is downstream of the detection zone and includes a limiting amount of a reagent which captures binding agent (e.g., an immobilised anti-binding agent antibody). The reagent is present at a level such that it retains the same amount of label which would bind to the detection zone for a threshold sample, with excess label continuing to migrate beyond the reference zone.

In these three types of device, therefore, a comparison between the detection zone and the reference zone is used to compare the sample with the threshold concentration. The detection:reference binding ratio can preferably be determined by eye. Close juxtaposition of the detection and reference zones is preferred in order to facilitate visual comparison of the signal intensities in the two zones.

In a fourth type of device, no reference zone is needed, but the detection zone is configured such that it gives an essentially on/off response, e.g., no signal is given below the threshold concentration but, at or above the threshold, signal is given.

In a fifth type of device, no reference zone is needed, but an external reference is used which corresponds to the threshold concentration. This can take various forms, e.g., a printed card against which the signal in the detection zone can be compared, or a machine reader which compares an absolute value measured in the detection zone (e.g., a calorimetric signal) against a reference value stored in the machine.

In some embodiments of the invention, the device includes a control zone downstream of the detection zone. This will generally be used to capture excess binding agent that passes through the detection and/or reference zones (e.g., using immobilized anti-binding agent antibody). When binding agent is retained at the control zone, this confirms that mobilization of the binding agent and migration through the device have both occurred. It will be appreciated that this function may be achieved by the reference zone.

In a preferred embodiment, the detection, reference and control zones are preferably formed on a nitrocellulose support.

Migration from the application zone to the detection zone will generally be assisted by a wick downstream of the detection zone to aid capillary movement. This wick is typically formed from absorbent material such as blotting or chromatography paper.

The device of the invention can be produced simply and cheaply, conveniently in the form of a dipstick. Furthermore, it can be used very easily, for instance by the home user.

The invention thus provides a device which can be used at home as a screen for cancer, such as ovarian cancer.

Kits for Diagnosing or Monitoring Gynecological Cancer

In one aspect, the present invention includes kits comprising the required elements for diagnosing or monitoring cancer. Preferably, the kits comprise a container for collecting biological fluid from a patient and an agent for detecting the presence of Bcl-2 or its encoding nucleic acid in the fluid. The components of the kits can be packaged either in aqueous medium or in lyophilized form.

The methods of the invention can be carried out using a diagnostic kit for qualitatively or quantitatively detecting Bcl-2 in a sample such as blood or urine. By way of example, the kit can contain binding agents (e.g., antibodies) specific for Bcl-2, antibodies against the antibodies labeled with an enzyme; and a substrate for the enzyme. The kit can also contain a solid support such as microtiter multi-well plates, standards, assay diluent, wash buffer, adhesive plate covers, and/or instructions for carrying out a method of the invention using the kit. In one embodiment, the kit includes one or protease inhibitors (e.g., a protease inhibitor cocktail) to be applied to the biological sample to be assayed (such as blood or urine).

Kits for diagnosing or monitoring gynecological cancer containing one or more agents that detect the Bcl-2 protein, such as but not limited to Bcl-2 antibodies, fragments thereof, or Bcl-2 binding partners, can be prepared. The agent(s) can be packaged with a container for collecting the biological fluid from a patient. When the antibodies or binding partner are used in the kits in the form of conjugates in which a label is attached, such as a radioactive metal ion or a moiety, the components of such conjugates can be supplied either in fully conjugated form, in the form of intermediates or as separate moieties to be conjugated by the user of the kit.

Kits containing one or more agents that detect Bcl-2 nucleic acid, such as but not limited to the full length Bcl-2 nucleic acid, Bcl-2 oligonucleotides, and pairs of Bcl-2 primers can also be prepared. The agent(s) can be packaged with a container for collecting biological samples from a patient. The nucleic acid can be in the labeled form or to be labeled form.

Other components of the kit may include but are not limited to, means for collecting biological samples, means for labeling the detecting agent (binding agent), membranes for immobilizing the Bcl-2 protein or Bcl-2 nucleic acid in the biological sample, means for applying the biological sample to a membrane, means for binding the agent to Bcl-2 in the biological sample of a subject, a second antibody, a means for isolating total RNA from a biological fluid of a subject, means for performing gel electrophoresis, means for generating cDNA from isolated total RNA, means for performing hybridization assays, and means for performing PCR, etc.

As used herein, the term "ELISA" includes an enzyme-linked immunoabsorbent assay that employs an antibody or antigen bound to a solid phase and an enzyme-antigen or enzyme-antibody conjugate to detect and quantify the amount of an antigen (e.g., Bcl-2) or antibody present in a sample. A description of the ELISA technique is found in Chapter 22 of the 4$^{th}$ Edition of Basic and Clinical Immunology by D. P. Sites et al., 1982, published by Lange Medical Publications of Los Altos, Calif. and in U.S. Pat. Nos. 3,654, 090; 3,850,752; and 4,016,043, the disclosures of which are herein incorporated by reference. ELISA is an assay that can be used to quantitate the amount of antigen, proteins, or other molecules of interest in a sample. In particular, ELISA can be carried out by attaching on a solid support (e.g., polyvinylchloride) an antibody specific for an antigen or protein of interest. Cell extract or other sample of interest such as urine can be added for formation of an antibody-antigen complex, and the extra, unbound sample is washed away. An enzyme-linked antibody, specific for a different site on the antigen is added. The support is washed to remove the unbound enzyme-linked second antibody. The enzyme-linked antibody can include, but is not limited to, alkaline phosphatase. The enzyme on the second antibody can convert an added colorless substrate into a colored product or can convert a non-fluorescent substrate into a fluorescent product. The ELISA-based assay method provided herein can be conducted in a single chamber or on an array of chambers and can be adapted for automated processes.

In these exemplary embodiments, the antibodies can be labeled with pairs of FRET dyes, bioluminescence resonance energy transfer (BRET) protein, fluorescent dye-quencher dye combinations, beta gal complementation assays protein fragments. The antibodies may participate in FRET, BRET, fluorescence quenching or beta-gal complementation to generate fluorescence, calorimetric or enhanced chemiluminescence (ECL) signals, for example.

These methods are routinely employed in the detection of antigen-specific antibody responses, and are well described in general immunology text books such as hnmunology by Ivan Roitt, Jonathan Brostoff and David Male (London: Mosby, c1998. 5th ed. and Immunobiology: Immune System in Health and Disease/Charles A. Janeway and Paul Travers. Oxford: Blackwell Sci. Pub., 1994), the contents of which are herein incorporated by reference.

Definitions

As used herein, the terms "cancer" and "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, and leukemia, as well as other cancers disclosed herein. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types are listed in Table 1.

TABLE 1

Examples of Cancer Types

| | |
|---|---|
| Acute Lymphoblastic Leukemia, Adult | Hairy Cell Leukemia |
| | Head and Neck Cancer |
| Acute Lymphoblastic Leukemia, Childhood | Hepatocellular (Liver) Cancer, Adult (Primary) |
| Acute Myeloid Leukemia, Adult | Hepatocellular (Liver) Cancer, Childhood |
| Acute Myeloid Leukemia, Childhood | (Primary) |
| Adrenocortical Carcinoma | Hodgkin's Lymphoma, Adult |
| Adrenocortical Carcinoma, Childhood | Hodgkin's Lymphoma, Childhood |
| | Hodgkin's Lymphoma During Pregnancy |
| AIDS-Related Cancers | Hypopharyngeal Cancer |
| AIDS-Related Lymphoma | Hypothalamic and Visual Pathway Glioma, Childhood |
| Anal Cancer | |
| Astrocytoma, Childhood Cerebellar | Intraocular Melanoma |
| Astrocytoma, Childhood Cerebral | Islet Cell Carcinoma (Endocrine Pancreas) |
| Basal Cell Carcinoma | Kaposi's Sarcoma |
| Bile Duct Cancer, Extrahepatic | Kidney (Renal Cell) Cancer |

TABLE 1-continued

Examples of Cancer Types

Bladder Cancer
Bladder Cancer, Childhood
Bone Cancer,
Osteosarcoma/Malignant Fibrous
Histiocytoma
Brain Stem Glioma, Childhood
Brain Tumor, Adult
Brain Tumor, Brain Stem Glioma,
Childhood
Brain Tumor, Cerebellar
Astrocytoma, Childhood
Brain Tumor, Cerebral
Astrocytoma/Malignant Glioma,
Childhood
Brain Tumor, Ependymoma,
Childhood
Brain Tumor, Medulloblastoma,
Childhood
Brain Tumor, Supratentorial
Primitive Neuroectodermal Tumors,
Childhood
Brain Tumor, Visual Pathway and
Hypothalamic Glioma, Childhood
Brain Tumor, Childhood
Breast Cancer
Breast Cancer, Childhood
Breast Cancer, Male
Bronchial Adenomas/Carcinoids,
Childhood
Burkitt's Lymphoma
Carcinoid Tumor, Childhood
Carcinoid Tumor, Gastrointestinal
Carcinoma of Unknown Primary
Central Nervous System Lymphoma,
Primary
Cerebellar Astrocytoma, Childhood
Cerebral Astrocytoma/Malignant
Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see
Mycosis Fungoides and Sézary
Syndrome
Endometrial Cancer
Ependymoma, Childhood
Esophageal Cancer
Esophageal Cancer, Childhood
Ewing's Family of Tumors
Extracranial Germ Cell Tumor,
Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial,
Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral
Astrocytoma
Glioma, Childhood Visual Pathway
and Hypothalamic Skin Cancer (Melanoma)
Skin Carcinoma, Merkel Cell
Small Cell Lung Cancer Kidney Cancer, Childhood
Laryngeal Cancer
Laryngeal Cancer, Childhood
Leukemia, Acute Lymphoblastic, Adult
Leukemia, Acute Lymphoblastic,
Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis
Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During
Pregnancy
Lymphoma, Primary Central Nervous
System
Macroglobulinemia, Waldenström's
Malignant Fibrous Histiocytoma of
Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with
Occult Primary
Multiple Endocrine Neoplasia Syndrome,
Childhood
Multiple Myeloma/Plasma Cell Neoplasm
Mycosis Fungoides
Myelodysplastic Syndromes
Myelodysplastic/Myeloproliferative
Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During
Pregnancy
Non-Small Cell Lung Cancer
Oral Cancer, Childhood
Oral Cavity Cancer, Lip and
Oropharyngeal Cancer
Osteosarcoma/Malignant Fibrous
Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive TABLE 1-continued Examples of Cancer Types

| | |
|---|---|
| Small Intestine Cancer | Neuroectodermal Tumors, Childhood |
| Soft Tissue Sarcoma, Adult | Pituitary Tumor |
| Soft Tissue Sarcoma, Childhood | Plasma Cell Neoplasm/Multiple Myeloma |
| Squamous Cell Carcinoma, see Skin Cancer (non-Melanoma) | Pleuropulmonary Blastoma |
| | Pregnancy and Breast Cancer |
| Squamous Neck Cancer with Occult Primary, Metastatic | Pregnancy and Hodgkin's Lymphoma |
| | Pregnancy and Non-Hodgkin's Lymphoma |
| Stomach (Gastric) Cancer | Primary Central Nervous System Lymphoma |
| Stomach (Gastric) Cancer, Childhood | |
| Supratentorial Primitive Neuroectodermal Tumors, Childhood | Prostate Cancer |
| | Rectal Cancer |
| T-Cell Lymphoma, Cutaneous, see Mycosis Fungoides and Sézary Syndrome | Renal Cell (Kidney) Cancer |
| | Renal Cell (Kidney) Cancer, Childhood |
| | Renal Pelvis and Ureter, Transitional Cell Cancer |
| Testicular Cancer | |
| Thymoma, Childhood | Retinoblastoma |
| Thymoma and Thymic Carcinoma | Rhabdomyosarcoma, Childhood |
| Thyroid Cancer | Salivary Gland Cancer |
| Thyroid Cancer, Childhood | Salivary Gland Cancer, Childhood |
| Transitional Cell Cancer of the Renal Pelvis and Ureter | Sarcoma, Ewing's Family of Tumors |
| | Sarcoma, Kaposi's |
| Trophoblastic Tumor, Gestational | Sarcoma, Soft Tissue, Adult |
| Unknown Primary Site, Carcinoma of, Adult | Sarcoma, Soft Tissue, Childhood |
| | Sarcoma, Uterine |
| Unknown Primary Site, Cancer of, Childhood | Sezary Syndrome |
| | Skin Cancer (non-Melanoma) |
| Unusual Cancers of Childhood | Skin Cancer, Childhood |
| Ureter and Renal Pelvis, Transitional Cell Cancer | |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), ultrasound, CT, and MRI, or by needle aspirations. The use of these latter techniques is more common in early detection. Molecular and phenotypic analysis of cancer cells within a tissue will usually confirm if the cancer is endogenous to the tissue or if the lesion is due to metastasis from another site.

A "sample" (biological sample) can be any composition of matter of interest from a human or non-human subject, in any physical state (e.g., solid, liquid, semi-solid, vapor) and of any complexity. The sample can be any composition reasonably suspecting of containing Bcl-2 that can be analyzed by the methods, devices, and kits of the invention. Preferably, the sample is a fluid (biological fluid). Samples can include human or animal samples. The sample may be contained within a test tube, culture vessel, multi-well plate, or any other container or supporting substrate. The sample can be, for example, a cell culture, human or animal tissue. Fluid homogenates of cellular tissues are biological fluids that may contain Bcl-2 for detection by the invention.

The "complexity" of a sample refers to the relative number of different molecular species that are present in the sample.

The terms "body fluid" and "bodily fluid", as used herein, refer to a composition obtained from a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions or mixtures containing homogenized solid material, such as feces, tissues, and biopsy samples.

The term "ex vivo," as used herein, refers to an environment outside of a subject. Accordingly, a sample of bodily fluid collected from a subject is an ex vivo sample of bodily fluid as contemplated by the subject invention. In-dwelling embodiments of the method and device of the invention obtain samples in vivo.

As used herein, the term "conjugate" refers to a compound comprising two or more molecules bound together, optionally through a linking group, to form a single structure. The binding can be made by a direct connection (e.g., a chemical bond) between the molecules or by use of a linking group.

As used herein, the terms solid "support", "substrate", and "surface" refer to a solid phase which is a porous or non-porous water insoluble material that can have any of a number of shapes, such as strip, rod, particle, beads, or multi-welled plate. In some embodiments, the support has a fixed organizational support matrix that preferably functions as an organization matrix, such as a microtiter tray. Solid support materials include, but are not limited to, cellulose, polysaccharide such as Sephadex, glass, polyacryloylmorpholide, silica, controlled pore glass (CPG), polystyrene, polystyrene/latex, polyethylene such as ultra high molecular weight polyethylene (UPE), polyamide, polyvinylidine fluoride (PVDF), polytetrafluoroethylene (PTFE; TEFLON), carboxyl modified teflon, nylon, nitrocellulose, and metals and alloys such as gold, platinum and palladium. The solid support can be biological, non-biological, organic, inorganic, or a combination of any of these, existing as particles, strands, precipitates, gels, sheets, pads, cards, strips, dipsticks, test strips, tubing, spheres, containers, capillaries, pads, slices, films, plates, slides, etc., depending upon the particular application. Preferably, the solid support is planar in shape, to facilitate contact with a biological sample such as urine, whole blood, plasma, serum, peritoneal fluid, or ascites fluid. Other suitable solid support materials will be readily apparent to those of skill in the art. The solid support can be a membrane, with or without a backing (e.g., polystyrene or polyester card backing), such as those available from Millipore Corp. (Bedford, Mass.), e.g., Hi-Flow™ Plus membrane cards. The surface of the solid support may contain reactive groups, such as carboxyl, amino, hydroxyl, thiol, or the like for the attachment of nucleic acids, proteins, etc. Surfaces on the solid support will sometimes, though not always, be composed of the same material as the support. Thus, the surface can be composed of any of a wide variety of materials, such as polymers, plastics, resins, polysaccharides, silica or silica-based materials, carbon, metals, inorganic glasses, membranes, or any of the aforementioned support materials (e.g., as a layer or coating).

As used herein, the terms "label" and "tag" refer to substances that may confer a detectable signal, and include, but are not limited to, enzymes such as alkaline phosphatase, glucose-6-phosphate dehydrogenase, and horseradish peroxidase, ribozyme, a substrate for a replicase such as QB replicase, promoters, dyes, fluorescers, such as fluorescein, isothiocynate, rhodamine compounds, phycoerythrin, phycocyanin, allophycocyanin, o-phthaldehyde, and fluorescamine, chemiluminescers such as isoluminol, sensitizers, coenzymes, enzyme substrates, radiolabels, particles such as latex or carbon particles, liposomes, cells, etc., which may be further labeled with a dye, catalyst or other detectable group.

As used herein, the term "receptor" and "receptor protein" are used herein to indicate a biologically active proteinaceous molecule that specifically binds to (or with) other molecules such as Bcl-2.

As used herein, the term "ligand" refers to a molecule that contains a structural portion that is bound by specific interaction with a particular receptor protein.

As used herein, the term "antibody" refers to immunoglobulin molecules and immunologically active portions (fragments) of immunoglobulin molecules, i.e., molecules that contain an antibody combining site or paratope. The term is inclusive of monoclonal antibodies and polyclonal antibodies.

As used here, the terms "monoclonal antibody" or "monoclonal antibody composition" refer to an antibody molecule that contains only one species of antibody combining site capable of immunoreacting with a particular antigen. A monoclonal antibody composition thus typically displays a single binding affinity for any antigen with which it immunoreacts. A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, *Nature*, 1975, 256:495-497, the disclosure of which is herein incorporated by reference. An exemplary hybridoma technology is described by Niman et al., *Proc. Natl. Acad. Sci. U.S.A.*, 1983, 80:4949-4953. Other methods of producing monoclonal antibodies, a hybridoma cell, or a hybridoma cell culture are also well known. See e.g., *Antibodies: A Laboratory Manual*, Harlow et al., Cold Spring Harbor Laboratory, 1988; or the method of isolating monoclonal antibodies from an immunological repertoise as described by Sasatry, et al., *Proc. Natl. Acad. Sci. USA*, 1989, 86:5728-5732; and Huse et al., *Science*, 1981, 246:1275-1281. The references cited are hereby incorporated herein by reference.

As used herein, a semi-permeable membrane refers to a bio-compatible material which is impermeable to liquids and capable of allowing the transfer of gases through it. Such gases include, but are not limited to, oxygen, water vapor, and carbon dioxide. Semi-permeable membranes are an example of a material that can be used to form a least a portion of an enclosure defining a flow chamber cavity. The semi-permeable membrane may be capable of excluding microbial contamination (e.g., the pore size is characteristically small enough to exclude the passage of microbes that can contaminate the analyte, such as cells). In a particular aspect, a semi-permeable membrane can have an optical transparency and clarity sufficient for permitting observation of an analyte, such as cells, for color, growth, size, morphology, imaging, and other purposes well known in the art.

As used herein, the term "bind" refers to any physical attachment or close association, which may be permanent or temporary. The binding can result from hydrogen bonding, hydrophobic forces, van der Waals forces, covalent, or ionic bonding, for example.

As used herein, the term "particle" includes insoluble materials of any configuration, including, but not limited to, spherical, thread-like, brush-like, and irregular shapes. Particles can be porous with regular or random channels inside. Particles can be magnetic. Examples of particles include, but are not limited to, silica, cellulose, Sepharose beads, polystyrene (solid, porous, derivatized) beads, controlled-pore glass, gel beads, magnetic beads, sols, biological cells, subcellular particles, microorganisms (protozoans, bacteria, yeast, viruses, and other infectious agents), micelles, liposomes, cyclodextrins, and other insoluble materials.

A "coding sequence" or "coding region" is a polynucleotide sequence that is transcribed into mRNA and/or translated into a polypeptide. For example, a coding sequence may encode a polypeptide of interest. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

As used herein, the term "polypeptide" refers to any polymer comprising any number of two or more amino acids, and is used interchangeably herein with the terms "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine.

The term "nucleotide" refers to a nucleoside having one or more phosphate groups joined in ester linkages to the sugar moiety. Exemplary nucleotides include nucleoside monophosphates, diphosphates and triphosphates.

The terms "polynucleotide", "nucleic acid molecule", and "nucleotide molecule" are used interchangeably herein and refer to a polymer of nucleotides joined together by a phosphodiester linkage between 5' and 3' carbon atoms. Polynucleotides can encode a polypeptide such as Bcl-2 polypeptide (whether expressed or non-expressed), or may be short interfering RNA (siRNA), antisense nucleic acids (antisense oligonucleotides), aptamers, ribozymes (catalytic RNA), or triplex-forming oligonucleotides (i.e., antigene), for example.

As used herein, the term "RNA" or "RNA molecule" or "ribonucleic acid molecule" refers generally to a polymer of ribonucleotides. The term "DNA" or "DNA molecule" or "deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog" or "nucleic acid analog", also referred to herein as an altered nucleotide/nucleic acid or modified nucleotide/nucleic acid refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. For example, locked nucleic acids (LNA) are a class of nucleotide analogs possessing very high affinity and excellent specificity toward complementary DNA and RNA. LNA oligonucleotides have been applied as antisense molecules both in vitro and in vivo (Jepsen J. S. et al., *Oligonucleotides*, 2004, 14(2): 130-146).

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA).

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state.

As used in this specification, the singular forms "a", "an", and "the" include plural reference unless the context clearly dictates otherwise. Thus, for example, a reference to "an antibody" includes more than one such antibody. A reference to "a molecule" includes more than one such molecule, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. Eds. (1991) IRL Press)), each of which are incorporated herein by reference in their entirety.

Following are examples that illustrate materials, methods, and procedures for practicing the invention. The examples are illustrative and should not be construed as limiting.

Materials and Methods

Patient cohort. With prior institutional approval, urine and blood samples were collected from normal healthy control volunteers (N=21), women with benign gynecologic disorders (N=35) and patients with ovarian cancer (N=34) at the H. Lee Moffitt Cancer Center. All except 8 specimens were collected prior to initial surgical debulking, while the latter 8 specimens presented with recurrent disease at the time of enrollment in the study. Paraffin blocks were identified, where possible, and the slides reviewed to confirm the histologic diagnosis according to FIGO scores. The medical records of these women were also reviewed and information regarding patient age, tumor type, stage, grade, size and surgical treatment abstracted where available.

Sample preparation. With patient informed consent, urine and plasma samples were collected from patients, anonymized and coded to protect patient identity, and released from the H. Lee Moffitt Cancer Center for this research protocol. All samples were kept in ice. Urine samples were treated with a standard protease inhibitor cocktail (80 µg/ml 4-(2 aminoethyl)-benzene sulfonyl fluoride, 200 µg/ml EDTA, 0.2 µg/ml leupeptin, 0.2 µg/ml pepstatin, Sigma Scientific, St. Louis, Mich.) and centrifuged at 3000×g. Urinary supernates and plasma samples were then aliquoted and stored at −20° C.

Enzyme-linked immunosorbant assay. To measure Bcl-2 levels in patients' urine, samples were assayed using the quantitative sandwich enzyme-linked immunosorbant assay (ELISA; R&D Systems, Minneapolis, Minn.) according to the manufacturer's instructions. To measure CA125 levels in subjects' plasma, samples were assayed by ELISA (BioQuant, San Diego, Calif.) according to the manufacturer's instructions. The enzymatic reactions were detected at 450 nm using a Dynex MRX plate reader (Dynex Technologies, Chantilly, Va.) and Bcl-2 results expressed as the mean absorbance of triplicate samples±S.E while CA125 results were expressed as the mean of duplicate samples.

Statistical analysis. Samples for Bcl-2 ELISA were run in triplicate and the data subjected to the Kruskal-Wallis test for normal distribution. Data were then analyzed by the Mann- Whitney U-test to determine statistical significance between samples from normal controls, patients with benign disease and ovarian cancer patients. Likewise, discrimination analyses using the SAS system were employed to determine appropriate membership in each group (normal vs. benign vs. cancer).

EXAMPLE 1

Urinary Bcl-2 Levels are Elevated in Ovarian Cancer Patients

Urine and blood were collected from 90 individuals with samples collected from normal controls (N=21), women with benign disease (N=35) and women with ovarian cancer (N=34). The latter category consisted of women diagnosed with endometriod (N=1), mucinous (N=7) as well as serous ovarian cancer (N=24) and primary peritoneal cancer, which is often related to ovarian cancer, (N=2). The samples collected from women with benign gynecologic disease consisted of women with benign cystic teratomas (N=2), simple cysts (N=10), leiomyomas (N=8), polycystic ovarian disease (N=1), ovarian adenofibromas (N=4), mucinous cystadenomas (N=2) and serous cystadenomas (N=8). Though this cohort comprises a small pilot study, it is representative of a typical clinical practice with regards to histology, grade and stage distribution.

Figure 1:
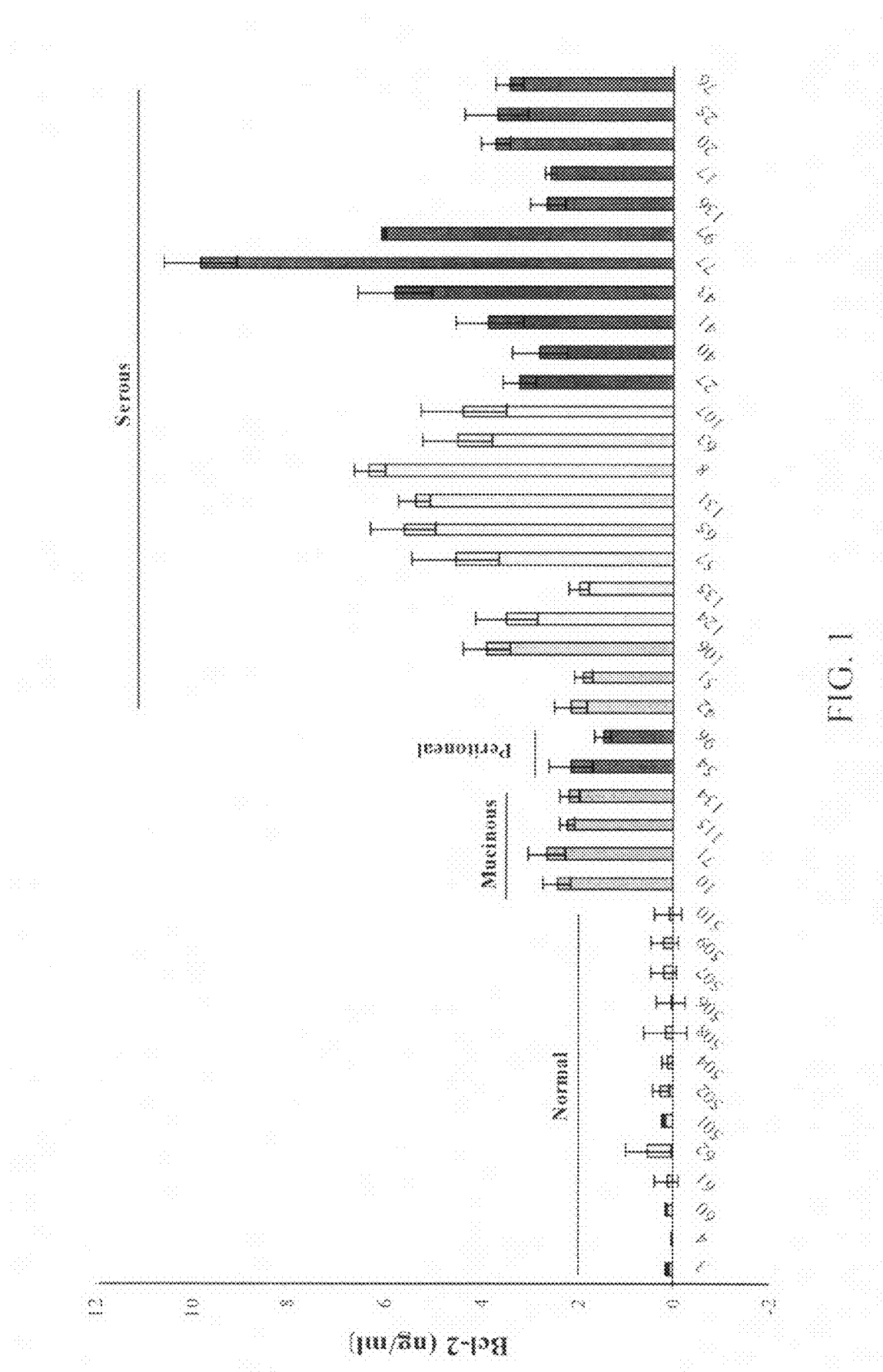
FIG. 1 is a histogram depicting urinary levels of Bcl-2. Urinary levels of Bcl-2 are higher in patients with ovarian cancer compared with normal healthy volunteers. Urine was collected from normal healthy volunteers and from patients with ovarian cancer (including histological subtypes serous, mucinous) and peritoneal cancer. Serous ovarian cancers were further subdivided into stage 1 (the first three bars on the left in the serous grouping), stage 2 (the next eight bars in the serous grouping (i.e., bars 4-11 from the left of the serous grouping)) and stage 3 (the eleven bars in the right-hand section of the serous grouping (i.e. bars 12-22 from the left of the serous grouping). The urine was tested in triplicate for Bcl-2 by ELISA (ELISA kits from Bender MedSystems, catalog #BMS244/3) and the results expressed as the average ng/ml Bcl-2±S.E. The data indicate consistently elevated levels of Bcl-2 in the urine of patients with cancer. Student t-test analysis revealed a statistical difference between normal and cancer specimens at $p<0.00001$.

To determine the potential suitability of urinary Bcl-2 levels as a new molecular marker for ovarian cancer, urine samples from the normal controls, women with benign gynecologic disease and patients with ovarian cancer specimens were screened by ELISA analyses (FIG. 1). The amount of urinary Bcl-2 was generally negligible (average 0.21 ng/ml) in normal control samples. In contrast, urinary Bcl-2 associated with ovarian and primary peritoneal cancer, was generally >10× (3.4 ng/ml) that found in normal control samples (FIG. 1A). No normal urine sample contained Bcl-2>1.8 ng/ml, while only 2 of the cancer samples exhibited Bcl-2 less than 1.8 ng/ml (1.12 ng/ml and 1.78 ng/ml).

Since serous carcinoma represents the majority of epithelial ovarian cancers, urinary Bcl-2 levels in patients with serous adenocarcinoma were examined by disease grade (FIG. 1A) and stage (FIG. 1B). Though there was a tendency for elevated Bcl-2 levels with increasing tumor grade and stage, the difference in Bcl-2 levels between tumor grade and stage was not statistically significant. Likewise, serum creatinine was measured at time of urine collection and indicated that urinary Bcl-2 levels were not related to renal dysfunction (data not shown). Of note, a single patient (#77) demonstrated extremely elevated urinary Bcl-2 levels (>9 ng/ml) in the absence of other notable clinical symptoms.

Figure 2:
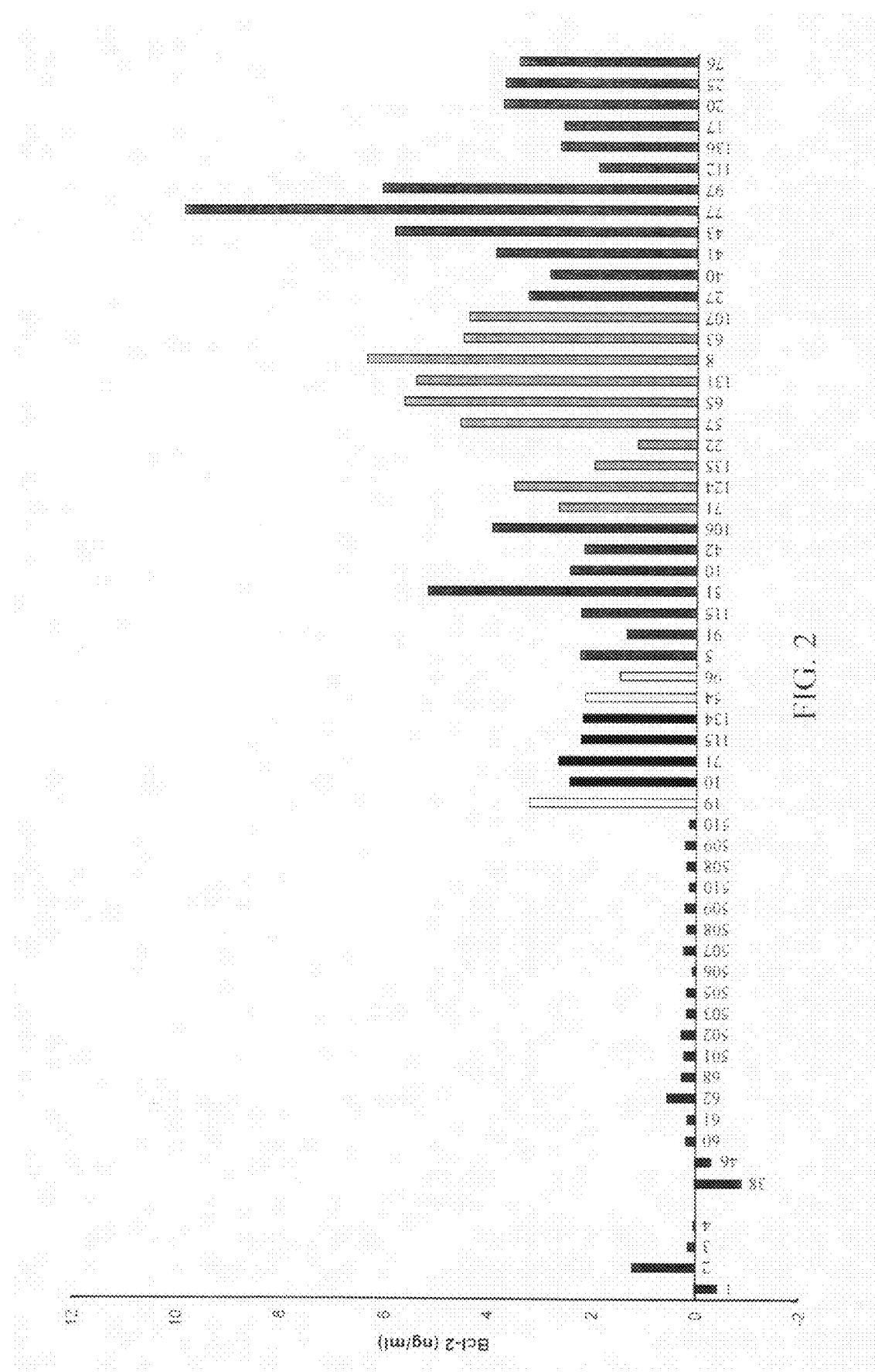
FIG. 2 is a histogram depicting urinary levels of Bcl-2 in normal and cancer patients. Additional urine specimens were collected from normal healthy volunteers and from patients with ovarian cancer (including histological subtypes endometroid, serous and mucinous) and peritoneal cancer. Serous ovarian cancers were further subdivided into stage 1 (7 left-most bars in serous grouping), stage 2 (bars 8-17 from the left in the serous grouping) and stage 3 (12 right-most bars in serous grouping). The urine was tested in triplicate for Bcl-2 by ELISA (ELISA kits from Bender Med Systems), the results expressed as the average ng/ml Bcl-2 and represent all the normal and the pre-surgical cancer urine specimens tested to date. In agreement with FIG. 1, the data indicate consistently elevated levels of Bcl-2 in the urine of patients with cancer. Student t-test analysis reveal a statistical difference between normal and cancer specimens at $p<0.00001$.

Table 2 summarizes the results presented in FIGS. 1 and 2 for average Bcl-2 levels in urine specimens. Numbers in parentheses indicate the number of samples in each respective group. Additionally, the data are grouped to show average Bcl-2 levels (ng/ml) between normal individuals and ovarian cancer histological subtypes, tumor grade and tumor stage. The data show that while the average level of Bcl-2 in the urine of healthy volunteers is 0.204 ng/ml, that from all cancer patients is generally 10× greater (3.12 ng/ml). In addition, urinary Bcl-2 levels appear strongly related to tumor stage and moderately related to tumor grade among serous ovarian cancers (the most frequently occurring type of ovarian cancer).

TABLE 2

Urinary Bcl-2 levels in Normal and Ovarian Cancer

| Sample | | Bcl-2 (ng/ml) |
|---|---|---|
| Normal (21) | | 0.204 |
| Endometriod (1) | | 3.168 |
| Mucinous (4) | | 2.35 |
| Peritoneal (2) | | 1.78 |
| Serous (29) | Grade 1 (7) | 2.76 |
| | Grade 2 (10) | 3.98 |
| | Grade 3 (12) | 3.94 |
| | Stage 1 (3) | 1.92 |
| | Stage 2 (4) | 3.23 |
| | Stage 3 (14) | 4.07 |
| | Stage 5 (8) | 4.04 |

EXAMPLE 2

Urinary Bcl-2 in Patients with Benign Gynecological Disease is not Elevated

ELISA measurement of urinary Bcl-2 from 35 women with benign gynecologic disease (urine collected just prior to patient's treatment) indicated Bcl-2 levels averaging 0.02 ng/ml with no samples>1.8 ng/ml Bcl-2, as shown in FIG. 8A. These benign diseases included benign teratomas, simple cists, leiomyomas, polystronic ovary, fibromas, and adenomas. These values were similar to normal controls, but significantly less than ovarian cancer samples suggesting that elevated urinary Bcl-2 levels greater than 1.8 ng/ml was associated with ovarian cancer.

The Kruskal-Wallis test was used to test the normal distribution of the data. Since the 'normal' group failed to meet normal distribution, likely due to small sampling number, the differences between groups were analyzed by the Mann-Whitney U-test. The results indicated no significant difference between normal and benign (p<0.5), but p<0.001 between normal and cancer or benign and cancer groups. A summary of urinary Bcl-2 level for this study group is presented in FIG. 8B. Likewise discrimination analyses using the SAS system revealed that the probability of appropriate membership in normal/benign or cancer group was >90%.

EXAMPLE 3

Urinary Bcl-2 does not Correlate with Patient Age or Tumor Size

Comparison of clinical parameters suggested that urinary Bcl-2 levels did not relate with patient age (see FIG. 5). Though the age range and average age of normal controls (29-81 yr, average 48.5±S.D. 12.7 yr) and women with benign gynecologic disease (28-84 yr, average 55.9±S.D. 13.9 yr) was somewhat lower that that of women with ovarian cancer (26-92 yr, average 62.2±S.D. 13.8 yr), the differences were not statistically significant in this study. Similarly, urinary Bcl-2 levels did not correlate with tumor size measured at debulking surgery (FIG. 6), ranging from microscopic to >10 cm and may reflect biologic variation between individuals or variation of tumor composition.

EXAMPLE 4

Urinary Bcl-2 detects ovarian cancer more accurately than CA125 in blood

To address whether elevated urinary Bcl-2 is a better diagnostic indicator for ovarian cancer than cancer antigen 125

(CA125), urinary Bcl-2 was compared with CA125 levels in 12 normal controls and 23 patients with ovarian cancer (FIGS. 4A and 4B). Of the patients examined, elevated urinary Bcl-2 associated with ovarian cancer detection was almost 100%. Elevated urinary Bcl-2 (>1.8 ng/ml) identified 17/17 patients with serous adenocarcinoma, 4/4 patients with mucinous ovarian cancer and ½ patients with primary peritoneal cancer as ovarian cancer positive (FIG. 4A). None of the normal controls had urinary Bcl-2 levels>1.8 ng/ml and were, then, correctly classified as cancer-negative. In contrast, blood levels of CA125>35 U/ml, the current standard for ovarian cancer detection, identified 13/17 or 76% of patients with serous adenocarcinoma (FIG. 4B). Likewise, CA125 analyses identified ¾ or 75% of patients with mucinous ovarian cancer, though CA125 levels in these patients ranged between 41-43 U/ml, and ½ or 50% of patients with primary peritoneal cancer as cancer positive. Elevated CA125 levels also incorrectly identified 2/12 or 16% of healthy individuals as cancer-positive suggesting that elevated urinary Bcl-2 appears to detect ovarian cancer more accurately than CA125.

EXAMPLE 5

Urinary Bcl-2 Decreases After Debulking Surgery

To further test the accuracy for high levels of urinary Bcl-2 to detect ovarian cancer, levels of urinary Bcl-2 were compared in 7 ovarian cancer patients immediately prior to (FIGS. 7A and 7B, black bars) and within 2 weeks following initial debulking surgery for removal of all visible tumor (white bars). For those patients where urine samples were collected before and after initial surgery, Bcl-2 levels decreased up to 100% following surgical removal of tumor suggesting that presence of tumor correlates well with elevated urinary Bcl-2 in ovarian cancer patients.

Currently, preclinical studies focus on the development of agents to inhibit Bcl-2, including antisense oligonucleotides and small molecular inhibitors of Bcl-2. Though such studies target Bcl-2 for therapeutic intervention, the present data indicate that quantification of urinary Bcl-2 by ELISA-based assays may provide a novel, safe, sensitive, specific and economical method for the detection of ovarian cancer that would benefit all women not only in the US, but worldwide including medically underserved geographical areas and especially women at high risk for developing ovarian cancer. Further, given that approximately 25,000 women are diagnosed with ovarian cancer annually in the US, urinary Bcl-2 detection of ovarian cancer in both early and late stages of disease would not only confirm the diagnosis of ovarian cancer, but could also potentially detect thousands of previously undiagnosed ovarian cancers. This is especially important for detection of ovarian cancer in early stages that account for less than 10% of diagnosed ovarian cancers, but where surgical debulking of the diseased ovary increases patient survival to over 90% and would be expected to reduce life long medical costs. Lastly, in addition to serving a novel diagnostic function, urinary levels of Bcl-2 can be used to monitor the presence of ovarian cancer throughout the course of disease which may impact therapeutic and prognostic outcome. Clearly, larger population studies are warranted to verify the potential for urinary levels of Bcl-2 to serve as a biomarker for ovarian cancer as well as investigations into the molecular mechanism(s) responsible for elevated urinary Bcl-2 in ovarian cancer. However, since there are no reports that employ either urinary detection or Bcl-2 as a biomarker for ovarian cancer, this pilot study suggests that measurement of urinary Bcl-2 by ELISA may provide an innovative, simple method to detect all ovarian cancers and, possibly, reduce the mortality of an insidious disease that kills thousands of women annually.

EXAMPLE 6

Urine Storage Conditions for Bcl-2 Testing

Studies examining the storage stability of urinary bcl-2 indicate that when samples are prepared with the addition of a cocktail of protease inhibitors these urine samples may be stored for over 1 year at −20° C. without loss of bcl-2 detection (see 'Control' & '−20° C.' in FIG. 11). This would be beneficial for individuals where it might be desirable to re-test previous samples with current ones. Alternately, these samples can also be stored at 4° C. for up to 4 days without adversely affecting detection of urinary Bcl-2. These are important results as they indicate that the time possibly required to transport patient urine samples (from potentially distant geographical areas) to a laboratory for Bcl-2 testing would not adversely affect the outcome of urinary bcl-2 detection if protease inhibitors are added to the urine samples and the urine samples are kept cold. However, reduced Bcl-2 was measured in samples stored at room temperature for 4 days and Bcl-2 could not be detected in urine samples stored at −80° C.; therefore, it appears prohibitive to store urinary samples for Bcl-2 detection at either room temperature or at −80° C.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method of accurately screening for ovarian cancer in a subject, comprising detecting the presence of Bcl-2 protein in a biological sample of urine from the subject using ELISA-based immunoenzymatic detection; and determining whether the level of Bcl-2 protein in the sample exceeds a predetermined threshold representing the level of urinary Bcl-2 protein in a non-cancerous individual, wherein a level of Bcl-2 protein above the pre-determined threshold level of urinary Bcl-2 protein of a non-cancerous individual is accurate to distinguish a subject having ovarian cancer from a non-cancerous individual.

2. The method of claim 1, wherein said detecting comprises:
   (a) contacting the biological sample with a binding agent that binds Bcl-2 protein to form a complex;
   (b) detecting the complex; and
   (c) correlating the detected complex to the amount of Bcl-2 protein in the sample.

3. The method of claim 2, wherein the binding agent is immobilized on a support.

4. The method. of claim 2, wherein the binding agent is a monoclonal or polyclonal antibody.

5. The method of claim 2, wherein said detecting of (b) further comprises linking or incorporating a label onto the binding agent.

6. The method of claim 1, further comprising detecting a biomarker of cancer other than Bcl-2 in the same biological sample or a different biological sample obtained from the subject, before, during, or after said detecting of Bcl-2.

7. The method of claim 6, wherein the biomarker of cancer is a biomarker of gynecological cancer.

8. The method of claim 6, wherein the biomarker is CA125, LPA, or OVXI.

9. The method of claim 1, wherein said subject is suffering from cancer, and wherein said detecting is performed at several time points at intervals, as part of a monitoring of the subject before, during, or after the treatment of the cancer.

10. The method of claim 1, further comprising comparing the level of Bcl-2 protein in the subject's biological sample with the level of Bcl-2 protein present in a normal control sample of urine from a non-cancerous individual, wherein a higher level of Bcl-2 protein in the subject's biological sample as compared to the level in the normal control sample is indicative of cancer.

11. The method of claim 1, wherein the subject is exhibiting no symptoms of cancer at the time said detecting is carried out.

12. The method of claim 1, wherein the subject is exhibiting one or more symptoms of cancer at the time said detecting is carried out.

13. The method of claim 1, wherein subject is exhibiting one or more of the symptoms selected from the group consisting of pelvic pain, abnormal vaginal bleeding, abdominal swelling or bloating, persistent back pain, persistent stomach upset, change in bowel or bladder pattern, pain during intercourse, unintentional weight loss of ten or more pounds, vulva or vaginal abnormality, change in the breast, and fatigue.

14. The method of claim 1, wherein the subject has an elevated CA125 level in the urine at the time of said detecting.

15. The method of claim 1, wherein the subject does not have an elevated CA125 level in the urine at the time of said detecting.

16. The method of claim 1, wherein said predetermined threshold is between 0.0 ng/ml and 2.0 ng/ml.

17. The method of claim 1, wherein said predetermined threshold is 1.8 ng/ml.

* * * * *

UNITED STATES PATENT AND TRADEMARK OFFICE
CERTIFICATE OF CORRECTION

PATENT NO.        : 8,034,549 B2
APPLICATION NO.   : 11/704408
DATED             : October 11, 2011
INVENTOR(S)       : Patricia A. Kruk It is certified that error appears in the above-identified patent and that said Letters Patent is hereby corrected as shown below:

Column 4,
Line 38, "grouping)." should read --grouping)).--.

Column 6,
Line 50, "bcl-2" should read --Bcl-2--.

Column 11,
Line 54, "and assistg" should read --and assist--.

Column 12,
Line 23, "bcl-2" should read --Bcl-2--.

Column 13,
Line 37, "chain F, molecule" should read --chain $F_v$ molecule--.

Column 15,
Line 56, "U.S. Pat. No. 5,3112,922" should read --U.S. Patent No. 5,312,922--.

Column 16,
Lines 14-15, "or rioncompetitive" should read --or noncompetitive--.

Column 19,
Lines 28-29, "the desired-amount" should read --the desired amount--.

Column 24,
Lines 62-63, "the kit includes one or protease" should read
--the kit includes one or more protease--.

Signed and Sealed this
Thirteenth Day of December, 2011

David J. Kappos
*Director of the United States Patent and Trademark Office*

CERTIFICATE OF CORRECTION (continued)
U.S. Pat. No. 8,034,549 B2

<u>Column 26,</u>
Line 17, "as hnmunology" should read --as Immunology--.

<u>Column 36,</u>
Line 53, "lower that that" should read --lower than that--.

<u>Column 38,</u>
Line 24, "bcl-2" should read --Bcl-2--.
Line 27, "bcl-2" should read --Bcl-2--.
Line 36, "bcl-2" should read --Bcl-2--.